United States Patent
Li et al.

(10) Patent No.: US 9,499,714 B2
(45) Date of Patent: Nov. 22, 2016

(54) CONTROLLED CROSSLINKING OF LATEX POLYMERS WITH POLYFUNCTIONAL AMINES

(71) Applicant: Ennis Paint, Inc, Thomasville, NC (US)

(72) Inventors: Haibo Li, High Point, NC (US); Kevin Newell, Thomasville, NC (US); Jeremy Cheek, Winston Salem, NC (US)

(73) Assignee: Ennis Paint, Inc., Thomasville, NC (US)

( * ) Notice: Subject to any disclaimer, the term of this patent is extended or adjusted under 35 U.S.C. 154(b) by 0 days.

(21) Appl. No.: 14/600,822

(22) Filed: Jan. 20, 2015

(65) Prior Publication Data

US 2015/0259562 A1   Sep. 17, 2015

Related U.S. Application Data

(63) Continuation-in-part of application No. 13/841,888, filed on Mar. 15, 2013, and a continuation-in-part of application No. PCT/US2014/030265, filed on Mar. 17, 2014.

(51) Int. Cl.

| | |
|---|---|
| *C09D 133/12* | (2006.01) |
| *C09D 7/12* | (2006.01) |
| *C09D 153/02* | (2006.01) |
| *C09D 5/02* | (2006.01) |
| *C07D 251/30* | (2006.01) |
| *C08K 5/3492* | (2006.01) |
| *C08F 220/14* | (2006.01) |
| *C07C 209/68* | (2006.01) |
| *C07C 215/08* | (2006.01) |
| *C07C 227/02* | (2006.01) |
| *C07C 229/16* | (2006.01) |
| *C09D 5/00* | (2006.01) |
| *C08K 5/103* | (2006.01) |
| *C08K 5/17* | (2006.01) |

(52) U.S. Cl.
CPC ........... *C09D 133/12* (2013.01); *C07C 209/68* (2013.01); *C07C 215/08* (2013.01); *C07C 227/02* (2013.01); *C07C 229/16* (2013.01); *C07D 251/30* (2013.01); *C08F 220/14* (2013.01); *C08K 5/34924* (2013.01); *C09D 5/024* (2013.01); *C09D 7/1233* (2013.01); *C09D 153/02* (2013.01); *E01F 9/518* (2016.02); *C08K 5/103* (2013.01); *C08K 5/17* (2013.01); *C08K 5/175* (2013.01); *C09D 5/00* (2013.01)

(58) Field of Classification Search
CPC .. C08L 63/00; C04B 41/4853; C09D 163/10
See application file for complete search history.

(56) References Cited

U.S. PATENT DOCUMENTS

| | | | |
|---|---|---|---|
| 4,265,745 A * | 5/1981 | Kawaguchi | B01D 69/125 210/491 |
| 4,755,623 A | 7/1988 | Dileone | |
| 4,772,680 A | 9/1988 | Noomen et al. | |
| 5,349,026 A | 9/1994 | Emmons et al. | |
| 5,498,659 A | 3/1996 | Esser | |
| 5,539,073 A | 7/1996 | Taylor et al. | |
| 5,681,907 A * | 10/1997 | Starner | C08G 59/184 525/526 |
| 5,939,514 A | 8/1999 | Brown et al. | |
| 6,028,141 A | 2/2000 | Singh et al. | |
| 6,262,169 B1 | 7/2001 | Helmer et al. | |
| 7,985,424 B2 | 7/2011 | Tomalia et al. | |

FOREIGN PATENT DOCUMENTS

| | | |
|---|---|---|
| EP | 555774 | 8/1993 |
| EP | 744540 A2 | 11/1996 |
| EP | 778317 A2 | 6/1997 |
| WO | 95/09209 A1 | 4/1995 |

* cited by examiner

*Primary Examiner* — Gregory Listvoyb
(74) *Attorney, Agent, or Firm* — Guerry L. Grune; ePatentManager

(57) ABSTRACT

The latex polymer compositions of the present invention exhibit latent crosslinking properties. Latent crosslinking in the polymers takes advantage of the fast interaction between the anionic latex charge and the cationic charge associated with polyfunctional amine crosslinkers. Once the latex is coated onto a substrate, the volatile base evaporates and the groups react to form a crosslinked coating with improved wash-off properties.

10 Claims, 4 Drawing Sheets

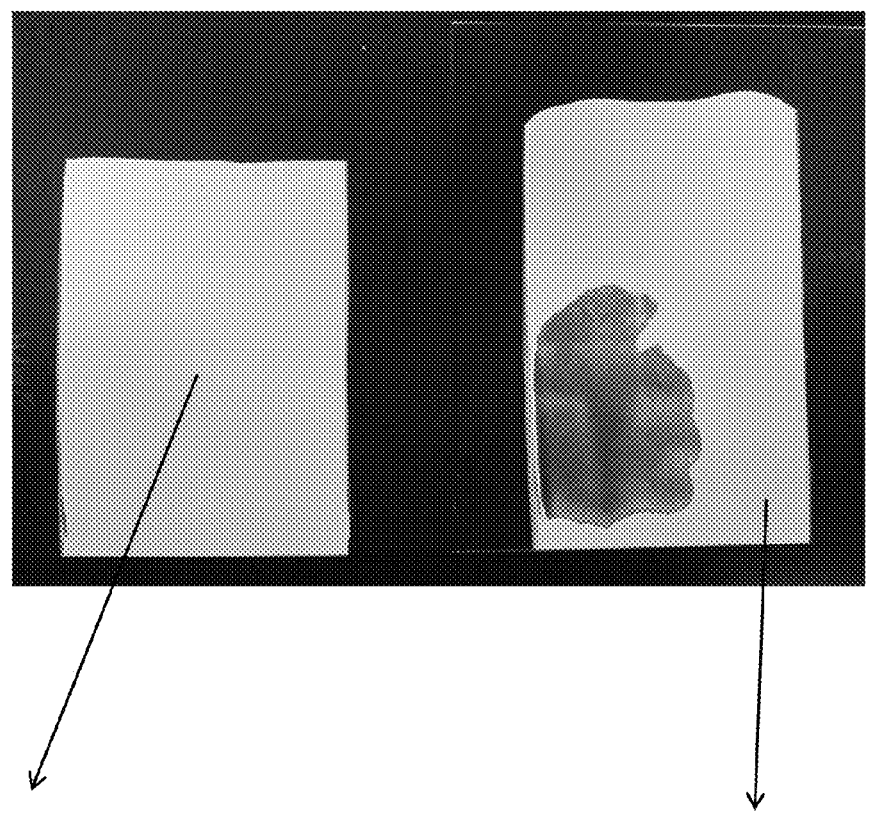
210   FIG. 2   220

CONTROLLED CROSSLINKING OF LATEX POLYMERS WITH POLYFUNCTIONAL AMINES

PRIORITY

This application is a Continuation-In-Part of and claims benefit under 35 USC 120 of U.S. Non-Provisional application Ser. No. 13/841,888 filed on Mar. 15, 2013, entitled "Fast Drying Aqueous Amine Free Coating Composition(s)". This application is also a Continuation-In-Part of PCT/US2014/030265, filed Mar. 17, 2014 and entitled "Fast Drying Aqueous Amine Free Coating Composition(s)". The above referenced applications are hereby incorporated in their entirety by reference for all purposes.

BACKGROUND

This disclosure covers the field of emulsion chemistry. In particular, it relates to distinct solution based polymerized latex compositions that are initially shelf stable emulsions prior to being used as coatings and/or paints. More specifically these latex compositions are kept shelf stable in the presence of a specific amount of ammonium hydroxide to maintain high pH in order to avoid premature interaction (pre-gelling) between latex particles leading to settling, and both inter and/or intraparticle crosslinking of the latex binders. These solutions are ammonia (NH3) rich (using ammonium hydroxide) and thus highly basic; therefore, when the NH3 evaporates quickly, the pH of the solutions are reduced as they are applied to surfaces. This process serves as a trigger for controlled crosslinking of the latex (binder) as it interacts with the polyfunctional amines of the present disclosure during application and drying. The pursuit of fast drying aqueous traffic paints requires there be strong and effective interactions between the latex binder and water-soluble polyfunctional amine crosslinkers, to ensure fast hardening at proper high build (in a single coat thick application) translating into corresponding water resistance.

In an increasing number of industries, aqueous coating compositions continue to replace traditional organic solvent-based coating compositions. Paints, inks, sealants, and adhesives, for example, previously formulated with organic solvents are now formulated as aqueous compositions. This reduces potentially harmful exposure to volatile organic compounds (VOC's) commonly found in solvent-based compositions. Migration from organic solvent-based to aqueous compositions allows for health and safety benefits, however, the aqueous coating compositions must meet or exceed the performance standards expected from solvent-based compositions. The need to meet or exceed the organic solvent based performance standards places a premium on the characteristics and properties of waterborne polymer compositions used in aqueous coating compositions.

The latex industry and specifically the latex-based traffic paint products have historically held a long established goal of developing effective "one-pack" (proper high build-in a single coat thick application)—or single step crosslinking systems. The ideal system allows for film formation prior to substantial crosslinking as the latex is applied to surfaces. The nature of this coating technology requires that it is stable when being stored and fast drying only when being applied. The structural make-up of these aqueous systems must be unreactive in the wet state, but very capable of ionic bonding (in ambient conditions) in the dry state; referred to hereinafter as latent crosslinking. The result of latent crosslinking would be a good film-forming latex with excellent hardness that is very resistant to water wash-off.

Much published art regarding various "one-pack" chemistries exists, including those based on epoxies (specifically glycidyl methacrylate), silanes, isocyanates, and carbonyls (including acetoacetoxy ethyl methacrylate, and acetoacetoxyethyl methacrylate—AAMA). Most of these publications and/or granted patents have demonstrated the presence of crosslinking by showing improved solvent resistance.

In order to increase the potlife (or shelf stability) of compositions containing acetoacetate and amine groups it has been known to block the amine groups of the polyamine with a ketone or aldehyde to form corresponding ketimine or aldimine compounds prior to mixing with an acetoacetate-functional polymer. Examples of such non-aqueous compositions are disclosed in U.S. Pat. No. 4,772,680. Even though improved stability may be achieved by specific aromatic aldimines, volatile by-products are still formed and the compositions have no application in waterborne coatings and are restricted to coatings using organic solvents as the carrier.

WO 95/09209 describes a crosslinkable coating composition comprising an aqueous film forming dispersion of addition polymer comprising acetoacetate functional groups and an essentially non-volatile polyamine having at least two primary amine groups and wherein the mole ratio of acetoacetate to primary amine groups is between 1:4 to 40:1.

EP 555,774 and WO 96/16998 describe the use of carboxylated acetoacetoxyethyl methacrylate latexes mixed with multifunctional amines (such as diethylene triamine) for a shelf-stable, one-component system. In EP 555,774, the system is stabilized by using vinyl acid polymerized with AAEM and the latex is "neutralized" with a polyamine. The patent teaches that the carboxyl groups should be 70 to 96 mol percent relative to the acetoacetoxy groups. WO 96/16998 similarly describes a polymerization process with the vinyl acid and AAEM being polymerized in the first stage.

EP 744,450 describes aqueous coating compositions containing acetoacetate functional polymers with a weight-averaged molecular weight of 100,000 or greater and which contain acetoacetate functional groups and acidic functional groups, and multifunctional amine.

EP 778,317 describes an aqueous self-crosslinkable polymeric dispersion comprising a polymeric component (a relatively hydrophobic polymer having a Hansch number >1.5, at least 5% of a carbonyl functional group capable of reacting with a nitrogen moiety, and at least 1% of a non-acidic functional group having hydrogen-bondable moieties); and a crosslinking agent comprising a nitrogen-containing compound having at least two nitrogen functional groups capable of reacting with a carbonyl functional moiety. Again it is reported that no gelation has taken place after ten days at 60° C.

U.S. Pat. No. 5,498,659 discloses a single-package aqueous polymeric formulation consisting essentially of an evaporable aqueous carrier, at least one polymeric ingredient having acid-functional pendant moieties able to form stable enamine structures, a non-polymeric polyfunctional amine having at least two amine functional moieties, and an effective amount of base for inhibiting gelation. It is stated in the patent that at least some of the crosslinking of the composition may take place in the liquid phase, possibly within one to four hours of adding the non-polymeric polyfunctional amine. It is postulated that addition of base to the reactor contents competes with the amine-functional moieties vis-à-vis the acetoacetoxy-type functional moieties, thereby reducing the degree of crosslinking and/or enhancing the colloidal stability of the polymer dispersion which forms when the crosslinking reaction takes place.

Geurink, et al., "Analytical Aspects and Film Properties of Two-Pack Acetoacetate Functional Latexes", Progress in Organic Coatings 27 (1996) 73-78, report that crosslinking of acetoacetate functional latexes with polyamine compounds is very fast, and that this crosslinking is hardly hindered by existing enamines. It is further stated that there are very strong indications that crosslinking takes place rapidly in the wet state, in or at the surface of the particles just after mixing of the components. They conclude that as a result of crosslinking in the particles, the film forming process is hampered.

In the publications described above, the usable pot life of the latex formulations is demonstrated by lack of sedimentation. It is quite possible, however, that crosslinking is taking place within each particle, without causing the latex to coagulate or gel (e.g. loss of colloidal stability). This type of intra-particle crosslinking (before drying) limits the ability of the latex to form a film upon drying. This in turn reduces the film integrity and performance of the polymer. Therefore, a need still exists for truly latent crosslinking systems—those in which intraparticle crosslinking is inhibited until after film formation. In particular, a need exists for one-pack, latent crosslinking systems which are useful in a wide range of latex applications that are simple and cost efficient. These would include decorative and protective coatings, adhesives, non-woven binders, textiles, paper coatings, traffic markings, inks, etc. In each case, the advantage would be a soft, ductile polymer that converts to a harder, more resistant latex film after drying.

In general, the following acronyms are used throughout the body this specification and provide information regarding chemical compounds and structures as follows;
TGIC=Triglycidyl isocyanurate
NPDGE=Neopentyl diglycidyl ether
AGE=Allyl glycidyl ether
BDGE=Butanediol diglycidyl ether
PEGDGE=Poly(ethylene glycol) diglycidyl ether
DMAPA=N,N-dimethyl amino propyl amine.
DEAPA=N,N-diethyl amino propyl amine.
DEA=diethyl amine
DAB=1,4-diaminobutane
MAA=methacrylic acid
tBHP=t-butyl hydroperoxide
BA=butyl acrylate
MMA=methyl methacrylate
MAA=methacrylic acid
SDS=sodium dodecyl sulfate
APS=ammonium persulfate

BRIEF DESCRIPTION OF THE DRAWINGS

FIG. 2 provides a photographic presentation of the water wash-off results of the latex paint formulations with and without crosslinker, as tested at 30 minutes dry time.

SUMMARY

Figure 1:
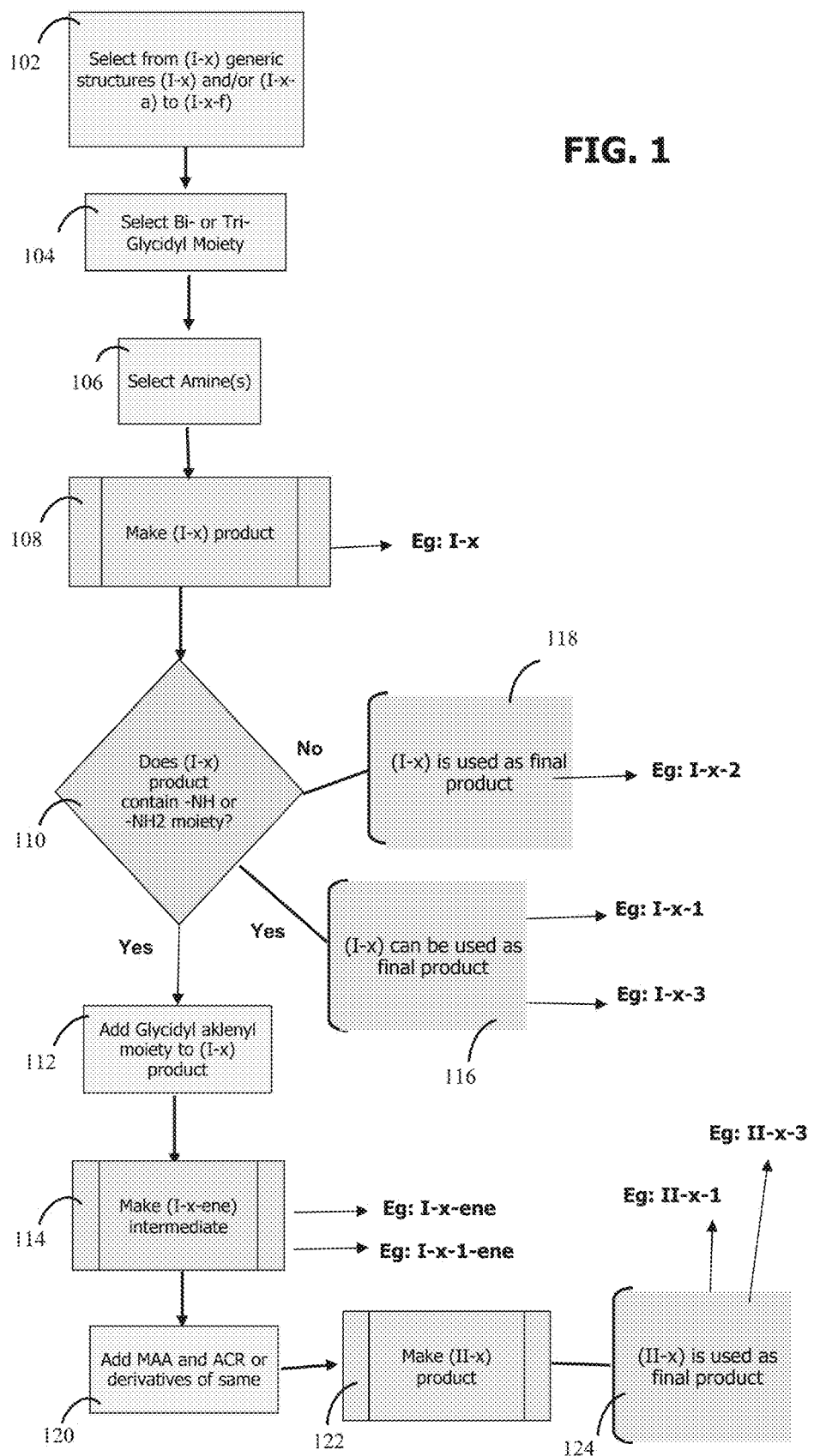
FIG. 1 is a flowchart providing various options for preparing polyfunctional amines of the present disclosure.

A first aspect of the present disclosure includes polyfunctional amine crosslinkers comprising recurring units derived from the reaction of one tri-glycidyl moiety and a single di-, or tri-functional amino monomers, or combination of mono/bi, mono/tri, mono/tetra, bi/bi, bi/tri, bi/tetra, tri/tri, tri/tetra, and tetra/tetra functional amino monomers resulting in a polyfunctional amine of formula (I-x):

$$\mathrm{-\!\!\!+\!\!J\underset{|}{\overset{R1}{-}}R2\!\!+\!\!\!_n\!\!-} \quad (\text{I-x})$$

Where the substituent J is the result of a ring-opening reaction during nucleophilic substitution of a bi- or tri-glycidyl moiety;

and wherein R1 is selected from the group consisting of: dimethyl amine, diethyl amine, diethanol amine, dipropyl amine, pyrrolidine, piperidine, 1-methyl piperazine, N,N,N-trimethyl-1,2-ethane diamine, N,N,N-triethyl-1,2-ethane diamine, N-methyl-N,N-diethyl-1,2-ethane diamine, N-ethyl-N,N-dimethyl-1,2-ethane diamine, N-methyl-N,N-diethyl-1,3-propane diamine, N-ethyl-N,N-dimethyl-1,3-propane diamine, methyl amine, ethyl amine, 1-propyl amine, ethanol amine, 2-propyl amine, 1-butyl amine, 2-butyl amine, 2-methyl-2-propyl amine, piperazine, N,N-dimethyl-ethyl diamine, N,N-diethyl-ethyl diamine, N,N-dimethyl propyl diamine, N,N-diethyl-propyl diamine, N,N-dimethyl amino propylene amine, N,N-dimethyl ethylene amine, N,N-diethyl amino propylene amine, N,N-diethyl-amino ethylene amine, amino ethyl-piperazine, N-methyl-1,2-ethane diamine, N-ethyl-1,2-ethane diamine, N-methyl-1,3-propane diamine, N-ethyl-1,3-propane diamine, 1,2-diamine ethane, 1,3-diamino propane, 1,4-diamino butane, cadaverine, cystamine, 1,6-diamino hexane, 1,2-diamine benzene, 1,3-diamino benzene, 1,4-diamino benzene, 1,4-diamino butanol, 4,4-diamino-3-hydroxy butanoic acid, 5-amino-1,3,3-trimethylcyclohexanemethylamine, 2,2'-oxybis ethanamine, alanine, and lysine;

and wherein R2 is selected from group consisting of methyl amine, ethyl amine, 1-propyl amine, ethanol amine, 2-propyl amine, 1-butyl amine, 2-butyl amine, 2-methyl-2-propyl amine, piperazine, N,N-dimethyl-ethyl diamine, N,N-diethyl-ethyl diamine, N,N-dimethyl propyl diamine, N,N-diethyl-propyl diamine, N,N-dimethyl amino propylene amine, N,N-dimethyl ethylene amine, N,N-diethyl amino propylene amine, N,N-diethylamino ethylene amine, amino ethyl-piperazine, N-methyl-1,2-ethane diamine, N-ethyl-1,2-ethane diamine, N-methyl-1,3-propane diamine, N-ethyl-1,3-propane diamine, 1,2-diamine ethane, 1,3-diamino propane, 1,4-diamino butane, cadaverine, cystamine, 1,6-diamino hexane, 1,2-diamine benzene, 1,3-diamino benzene, 1,4-diamino benzene, 1,4-diamino butanol, 4,4-diamino-3-hydroxy butanoic acid, 5-amino-1,3,3-trimethylcyclohexanemethylamine, 2,2'-oxybis ethanamine, alanine, lysine;
and where R1 is equal to or different than R2;
and where n is a number from 10 to 100.

More specifically, the polyfunctional amines are selected from one of the general structures of formulae (I-x) and/or (I-x-a) to (I-x-f):

$$\mathrm{-\!\!\!+\!\!J\underset{|}{\overset{R1}{-}}R2\!\!+\!\!\!_n\!\!-} \quad (\text{I-x})$$

-continued

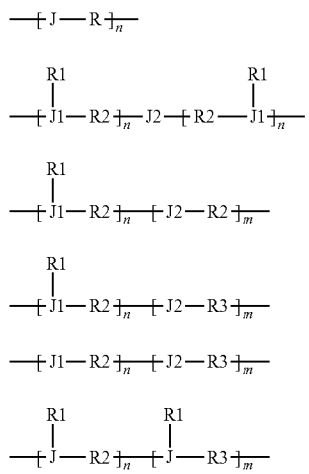

(I-x-a)
(I-x-b)
(I-x-c)
(I-x-d)
(I-x-e)
(I-x-f)

wherein substituents J, J1, and J2 are the result of a ring-opening reaction during nucleophilic substitution of a bi- or tri-glycidyl moiety;
and wherein J is equal to or different than J1 and J2;
and wherein J1 is equal to or different than J2;
and wherein R1 is selected from the group consisting of: dimethyl amine, diethyl amine, diethanol amine, dipropyl amine, pyrrolidine, piperidine, 1-methyl piperazine, N,N,N-trimethyl-1,2-ethane diamine, N,N,N, triethyl-1,2-ethane diamine, N-methyl-N,N-diethyl-1,2-ethane diamine, N-ethyl-N,N-dimethyl-1,2-ethane diamine, N-methyl-N,N-diethyl-1,3-propane diamine, N-ethyl-N,N-dimethyl-1,3-propane diamine, methyl amine, ethyl amine, 1-propyl amine, ethanol amine, 2-propyl amine, 1-butyl amine, 2-butyl amine, 2-methyl-2-propyl amine, piperazine, N,N-dimethyl-ethyl diamine, N,N-diethyl-ethyl diamine, N,N-dimethyl propyl diamine, N,N-diethyl-propyl diamine, N,N-dimethyl amino propylene amine, N,N-dimethyl ethylene amine, N,N-diethyl amino propylene amine, N,N-diethyl-amino ethylene amine, amino ethyl-piperazine, N-methyl-1,2-ethane diamine, N-ethyl-1,2-ethane diamine, N-methyl-1,3-propane diamine, N-ethyl-1,3-propane diamine, 1,2-diamine ethane, 1,3-diamino propane, 1,4-diamino butane, cadaverine, cystamine, 1,6-diamino hexane, 1,2-diamine benzene, 1,3-diamino benzene, 1,4-diamino benzene, 1,4-diamino butanol, 4,4-diamino-3-hydroxy butanoic acid, 5-amino-1,3,3-trimethylcyclohexanemethylamine, 2,2'-oxybis ethanamine, alanine, and lysine;
and R2 and R3 are selected from group consisting of methyl amine, ethyl amine, 1-propyl amine, ethanol amine, 2-propyl amine, 1-butyl amine, 2-butyl amine, 2-methyl-2-propyl amine, piperazine, N,N-dimethyl-ethyl diamine, N,N-diethyl-ethyl diamine, N,N-dimethyl propyl diamine, N,N-diethyl-propyl diamine, N,N-dimethyl amino propylene amine, N,N-dimethyl ethylene amine, N,N-diethyl amino propylene amine, N,N-diethylamino ethylene amine, amino ethyl-piperazine, N-methyl-1,2-ethane diamine, N-ethyl-1,2-ethane diamine, N-methyl-1,3-propane diamine, N-ethyl-1,3-propane diamine, 1,2-diamine ethane, 1,3-diamino propane, 1,4-diamino butane, cadaverine, cystamine, 1,6-diamino hexane, 1,2-diamine benzene, 1,3-diamino benzene, 1,4-diamino benzene, 1,4-diamino butanol, 4,4-diamino-3-hydroxy butanoic acid, 5-amino-1,3,3-trimethyl-cyclohexanemethylamine, 2,2'-oxybis ethanamine, alanine, lysine;
and wherein R1 is equal to or different than R2 and R3;
and wherein R2 is equal to or different than R3;
and where n is an number 10 to 100;
and where m is an number equal to or different than n.

Any polyfunctional amine shown above can be used in latex paint formulas as crosslinkers. In addition, the polyfunctional amine crosslinker of any type formula (I-x) bearing —NH or —NH$_2$ groups with repeating units, n, can be further treated with glycidyl alkenyl compounds, favorably allyl glycidyl ether,
and the polyfunctional amine of any formulae (I-x) and/or (I-x-a) to (I-x-f) must carry a —NH or —NH2 group, for further reaction with a glycidyl alkenyl compound for the introduction of an alkene group as shown below;

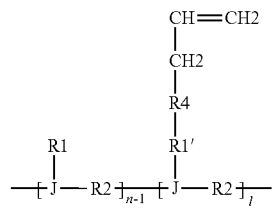

(I-x-ene)

and wherein the reaction between the polyfunctional amine selected from Formulae (I-x) and/or (I-x-a) to (I-x-f) and allyl glycidyl ether occurs via the amino-glycidyl linkage;
and wherein the addition of the allyl reactive group to the structure of formula (I-x) occurs only once per molecule.

The polyfunctional amine crosslinkers are capable of providing the structure of formula (I-x-ene) which when reacted with MAA and ACR forms copolymers of formula II-x;

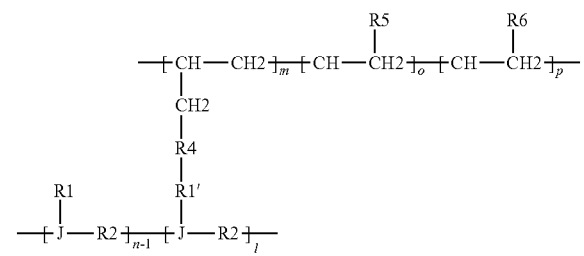

(II-x)

wherein J is the result of a ring-opening reaction during nucleophilic substitution of a bi- or tri-glycidyl moiety;
and wherein R1, and R2 are selected from the group consisting of: methyl amine, ethyl amine, 1-propyl amine, ethanol amine, 2-propyl amine, 1-butyl amine, 2-butyl amine, 2-methyl-2-propyl amine, piperazine, N,N-dimethyl-ethyl diamine, N,N-diethyl-ethyl diamine, N,N-dimethyl propyl diamine, N,N-diethyl-propyl diamine, N,N-dimethyl amino propylene amine, N,N-dimethyl ethylene amine, N,N-diethyl amino propylene amine, N,N-diethylamino ethylene amine, amino ethyl-piperazine, N-methyl-1,2-ethane diamine, N-ethyl-1,2-ethane diamine, N-methyl-1,3-propane diamine, N-ethyl-1,3-propane diamine, 1,2-diamine ethane, 1,3-diamino propane, 1,4-diamino butane, cadaverine, cystamine, 1,6-diamino hexane, 1,2-diamine benzene, 1,3-diamino benzene, 1,4-diamino benzene, 1,4-diamino butanol, 4,4-diamino-3-hydroxy butanoic acid, 5-amino-1, 3,3-trimethylcyclohexanemethylamine, 2,2'-oxybis ethanamine, alanine, and lysine;

and wherein R1 is equal to or different than R2;

and wherein R1' is the deprotonated R1 with proton loss at the NH or $NH_2$ site;

and wherein R4 is the connecting group between polyamine body and the alkene functionality. If AGE is employed in this preparation, the connecting group is —$CH_2CH(OH)CH_2O$—. Variations in R4 may be created from each different connecting glycidyl alkenyl compound. Potentially, the connecting glycidyl alkenyl compound can be selected from one of the following: allyl glycidyl ether, vinyl glycidyl ether, vinyl cyclohexene oxide, glycidyl methacrylate, glycidyl acrylate, glycidyl acrylamide, and glycidyl methacrylamide.

and wherein n–1 is an number from four to nineteen;
and wherein m is an number from 1 to 100;
and wherein o is an number from 1 to 100;
and wherein p is an number from 1 to 100;
and wherein repeating unit carrying R5 is resulted from polymerization of a water soluble monomer having a carbon to carbon double bond, C=C, preferably an acrylic acid or acrylic acid derivative;
and wherein repeating unit carrying R6 is resulted from polymerization of a water soluble monomer having a carbon to carbon double bond, C=C, preferably acrylamide or a derivative of acrylamide;
and where the resulting structure is greater than or equal to 50,000 Daltons.

As illustrated in the flowchart [100] of FIG. 1, the polyfunctional amine latex crosslinker compositions are selected from at least one compound from the group consisting of Formulae (I-x) and/or (I-x-a to I-x-f) [102], composed of a bi- or tri-glycidyl moiety [104] and amine(s) [106]. I-x for the purposes of this disclosure is shown (but is not limited a limiting example) forming structural compounds (I-x-1), (I-x-2), and (I-x-3). These three structures are developed from a one-step synthesis creating the (I-x) products (structural compounds) [108] and do not include any C=C bonds. If selected for use as a final product, the one-step (I-x) products can be used with no further treatment. Polyfunctional amine (I-x) products [108] containing an —NH or —$NH_2$ moiety [110] can be further treated to form final two-step process products [124] or be used without further treatment as a final —NH or —$NH_2$ containing one-step product [116]. Polyfunctional amine (I-x) products [108] without an —NH or —NH2 moiety [110] can only be used as a final one-step product [118].

When the (I-x) structural compound [108], is reacted with AGE (or any of the provided glycidyl alkenyl compounds) [112] the result is the formation of the I-x-ene intermediate structure [114] (represented as I-x-ene), but can be prepared from any of the I-x and/or I-x-a to I-x-f structures [102] shown that include either the —NH or —$NH_2$ moieties [110]. The I-x-ene intermediate structure [114] is prepared so that one can add MAA and ACR (or derivatives thereof) [120] to increase molecular weight.

Alternatively a two-step process which forms the crosslinker structural compounds II-x-1 and II-x-3 requires the formation of the one step products (I-x-1 or I-x-3) that include —NH or —$NH_2$ moieties (side groups) [110] and the addition of AGE (or other glycidyl alkenyl compounds) [112] resulting in the intermediate I-x-ene product [114]. This I-x-ene product [114] is followed by the addition of acrylamide and MAA or (derivatives of either) [120] to provide the (II-x) products [122] which are examples of final two-step process products [124]. The structural features of each of these compounds are provided below;

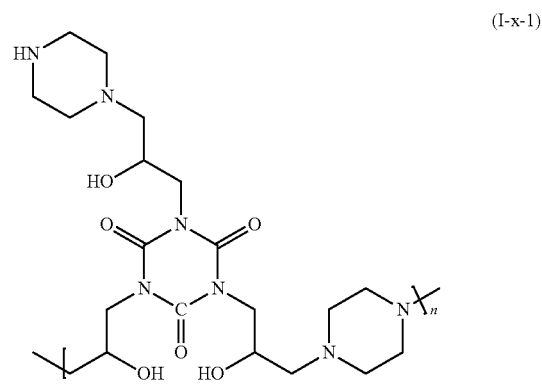

(I-x-1)

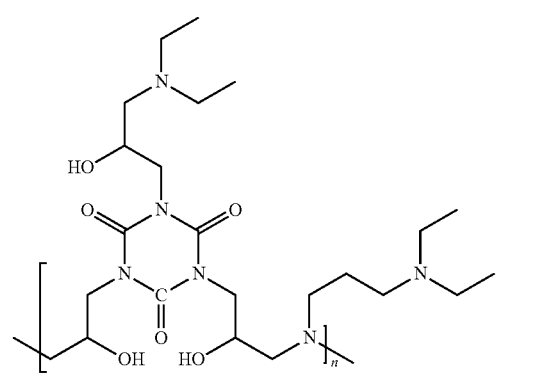

(I-x-2)

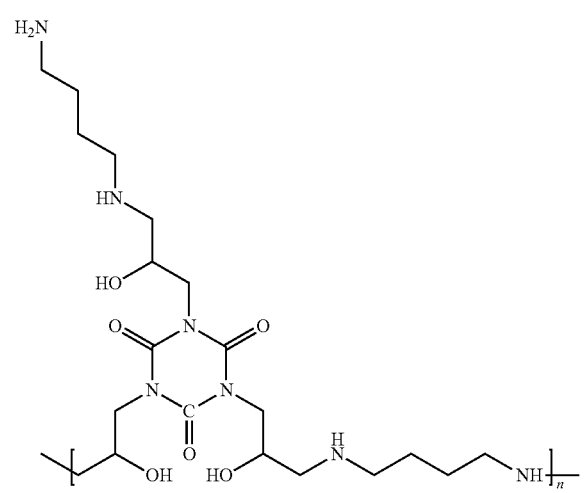

(I-x-3)

In a further embodiment, the polyfunctional amine latex crosslinker compositions can also be an intermediate formed prior to the polymerization prepared with the addition of allyl glycidyl ether (AGE) comprising formula (I-x-1);

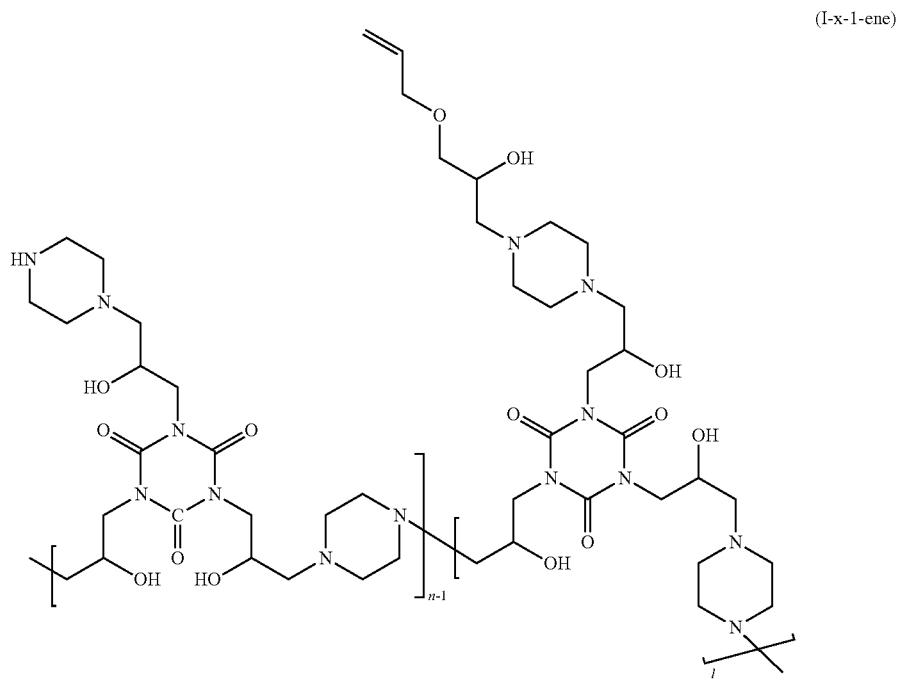
(I-x-1-ene)
The polyfunctional amine latex crosslinker intermediate composition above when reacted with both methyl acrylic acid (MAA) and acrylamide (ACR) results in polymers of structures (II-x-1) and (II-x-3).
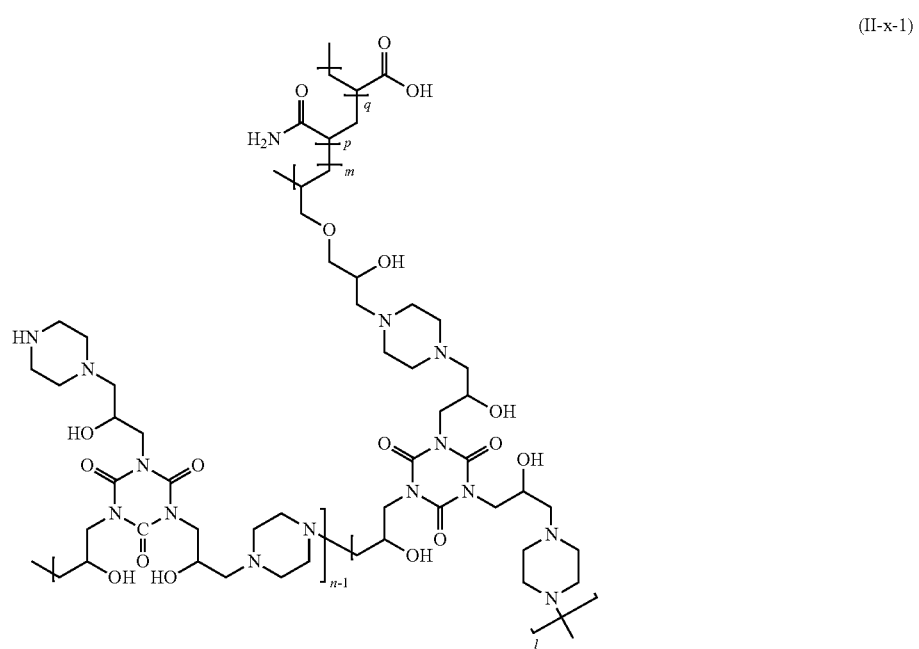
(II-x-1)

-continued

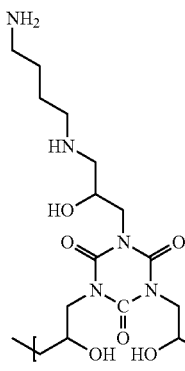
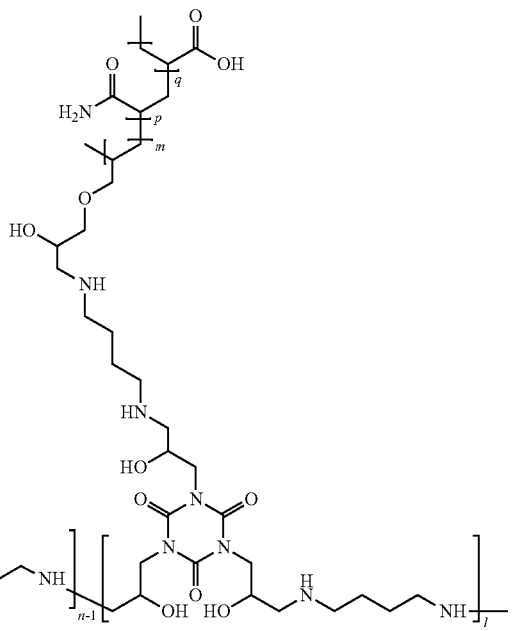

(II-x-3)

The structures (II-x-1) and (II-x-3) can also result in producing polymeric structures with molecular weights higher than those of the oligomers of the same compositional structures of (II-x-1) and (II-x-3).

Complete paint formulations utilizing both a latex and the polyfunctional amines described and provided above is also a subject of the present disclosure. The paint additionally includes at least one dispersant, defoamer, surfactant, biocide, ammonia, rheology agent, pigment, solvent, coalescent, and water. The paint can be used as traffic paint for a pavement surface. Additionally, when the paint formulation is applied to pavement surfaces crosslinking of the paint occurs and early water resistance at 15-45 minutes can occur.

DETAILED DESCRIPTION

The present invention provides polyfunctional amine crosslinkers for use in latex polymer compositions and the latex polymer compositions containing them. The latex polymer compositions of the present invention typically include, but are not limited to, latexes, dispersions, microemulsions, or suspensions. The latex polymer compositions of the present invention may be stored at room temperature or moderately above room temperature (e.g., about 50 to 60° C.) and provide adhesion and crosslinking upon film formation when applied to a substrate. A film or coating formed with polymers of the present invention may be cured at room temperature (ambient cure) or at elevated temperatures (thermal cure).

The latex polymer binders used to prepare the waterborne polymer composition of the present disclosure are generally prepared as particles. The particles may be structured or unstructured. Structured particles include, but are not limited to, core/shell particles and gradient particles. The average polymer particle size may range from about 100 to about 300 nm.

The polymer particles have a spherical shape. In one embodiment, the spherical polymeric particle may have a core portion and a shell portion. The core/shell polymer particles may also be prepared in a multi-lobe form, a peanut shell, an acorn form, or a raspberry form. It is further preferred in such particles that the core portion comprises about 20 to about 80 of the total weight of said particle and the shell portion comprises about 80 to about 20 of the total weight volume of the particle.

The present disclosure includes compositions and methods for the preparation of water soluble polymeric and oligomeric polyfunctional amines for use as crosslinking agents in solutions of fast drying latex emulsions. The oligomeric/polymeric polyfunctional amine synthesized in a single step reaction by reacting bi- or tri-functional glycidyl and/or glycidyl isocyanurate groups with water soluble bi-, tri- and tetra-amines as the starting materials (reactants) serve as crosslinkers for latex paints. Oligomeric/polymeric polyfunctional amines with lower molecular weight can be prepared from the same chemistry and the resulted product can be combined with glycidyl alkenyl compounds, allyl glycidyl ethers (AGE) is most favorable, in a two-step reaction process to form additional oligomers which are capable of molecular weight building via free radical initiated polymerization. The definition of whether the chemical structure is an oligomer or polymer depends on the final weight average molecular weight (as determined primarily by the number and molecular weight) of the repeating structural monomeric chains.

The fast drying and proper curing due to crosslinking of the latex emulsion is triggered by rapid evaporation of $NH_3$ in the paint formulation concurrent with a rise in the pH of the emulsion during and after being applied to the intended surface. The interaction of the latex binder together with the crosslinking polyfunctional amine (primarily) oligomers results in fast dry traffic latex polymers (as paint or coatings) which harden quickly. These polymeric/oligomeric amines provide for excellent water (especially rain water) resistant films due in part due to their rapid cure times. The waterborne fast dry paint serves as road and pavement marking paint which can be used to mark lines or symbols on roads, parking lots, and walkways etc.

In the present disclosure, the polyfunctional oligomeric amines possess structural chain extending groups that allow for tailoring the molecular weight of the crosslinker. More specifically, the polyfunctional oligomeric/polymeric amine examples of this disclosure are comprised of di or tri glycidyl monomers, or combination of di/di, di/tri, or tri/tri glycidyl monomers and either of bi, tri or tetra amino monomers, and combination of bi/bi, bi/tri, bi/tetra, mono/bi, mono/tri, mono/tetra, bi/tetra, tri/tetra functional amino monomers.

The synthesis of the final crosslinker can be completed as a one-step or two-step process. The one-step process provides novel crosslinkers resulting from glycidyl monomer/glycidyl monomers and amino monomer/amino monomers. The two-step process provides the crosslinkers of the one-step process that have been further reacted with AGE and polymerized or copolymerized with methacrylic acid (MAA) and an acrylamide, forming complex structures with pendant polyfunctional polymeric/oligomeric amine groups Selection of Monomers Triglycidyl isocyanurate is the only trifunctional glycidyl monomer used in this disclosure. Diglycidyl monomers include: polypropylene glycol) diglycidyl ether, poly(ethylene glycol) diglycidyl ether, resorcinol glycidyl ether, neopentyl diglycidyl ether, and butanediol diglycidyl ether. The glycidyl monomer(s) employed in the disclosure can be single or in combination.

Amine monomers employed in this work can be bi-, tri- or tetra-monomers or combinations of mono/bi, mono/tri, mono/tetra, bi/bi, bi/tri, bi/tetra, tri/tri, tri/tetra and tetra/tetra functional monomers. In amine monomers, the number of functionalities is defined by the number of N—H bonds.

A full list of mono-functional amine monomers include: dimethyl amine, diethyl amine, diethanol amine, dipropyl amine, pyrrolidine, piperidine, 1-methyl piperazine, N,N,N-trimethyl-1,2-ethane diamine, N,N,N, triethyl-1,2-ethane diamine, N-methyl-N,N-diethyl-1,2-ethane diamine, N-ethyl-N,N-dimethyl-1,2-ethane diamine, N-methyl-N,N-diethyl-1,3-propane diamine, and N-ethyl-N,N-dimethyl-1,3-propane diamine, A full list of bi-functional amine monomers includes: methyl amine, ethyl amine, 1-propyl amine, ethanol amine, 2-propyl amine, 1-butyl amine, 2-butyl amine, 2-methyl-2-propyl amine, piperazine, N,N-dimethyl-ethyl diamine, N,N-diethyl-ethyl diamine, N,N-dimethyl propyl diamine, N,N-diethyl-propyl diamine, N,N-dimethyl amino propylene amine, N,N-dimethyl ethylene amine, N,N-diethyl amino propylene amine, and N,N-diethylamino ethylene amine.

A full list of tri-functional amine monomers includes: amino ethyl-piperazine, N-methyl-1,2-ethane diamine, N-ethyl-1,2-ethane diamine, N-methyl-1,3-propane diamine, and N-ethyl-1,3-propane diamine.

A full list of tetra-functional amine monomers includes: 1,2-diamine ethane, 1,3-diamino propane, 1,4-diamino butane, cadaverine, cystamine, 1,6-diamino hexane, 1,2-diamine benzene, 1,3-diamino benzene, 1,4-diamino benzene, 1,4-diamino butanol, 4,4-diamino-3-hydroxy butanoic acid, 5-amino-1,3,3-trimethylcyclohexanemethylamine, 2,2'-oxybis ethanamine, alanine, and lysine.

Creation of an alkenyl functional oligomeric polyamine for 2-step free radical polymerization involves a reaction between the corresponding oligomeric polyfunctional amine and glycidyl alkenyl compounds. A full list of glycidyl alkenyl compounds includes: allyl glycidyl ether, vinyl glycidyl ether, vinyl cyclohexene oxide, glycidyl methacrylate, glycidyl acrylate, glycidyl acrylamide, glycidyl methacrylamide.

Reaction Type I: One-Step Process

A first aspect of the present disclosure concerns polyfunctional amine crosslinkers comprising recurring units derived from the reaction of one tri-glycidyl moiety and a single di-, or tri-functional amino monomers, or combination of mono/bi, mono/tri, mono/tetra, bi/bi, bi/tri, bi/tetra, tri/tri, tri/tetra and tetra/tetra functional amino monomers resulting in a polyfunctional amine of formula (I-x):

(I-x)

Where the substituent J is the result of a ring-opening reaction during nucleophilic substitution of a bi- or tri-glycidyl moiety;
and wherein R1 is selected from the group consisting of all possible mono-functional, bi-functional, tri-functional or tetra-functional amines, as provided above;
and wherein R2 is selected from the group of all possible bi-functional, tri-functional or tetra-functional amines;
and where R1 is equal to or different than R2;
and where n is an number 10 to 100.

Further possible structures for providing polyfunctional amines using a one-step synthetic process are provided in general formulae (I-x) and/or (I-x-a) to (I-x-f):

(I-x)

(I-x-a)

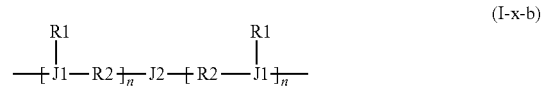

(I-x-b)

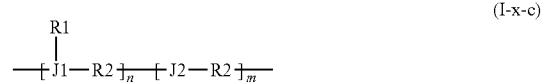

(I-x-c)

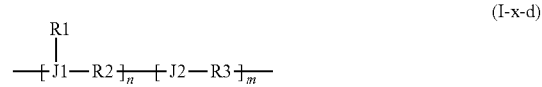

(I-x-d)

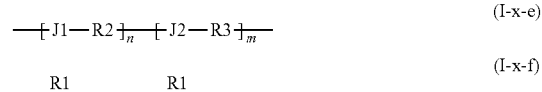

(I-x-e)

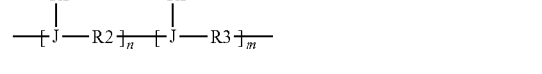

(I-x-f)

Where the substituents J, J1, and J2 are the result of a ring-opening reaction during nucleophilic substitution of a bi- or tri-glycidyl moiety, and wherein J is equal to or different than J1 and J2;
and wherein J1 is equal to or different than J2;
and wherein R1 is selected from the group consisting of all possible mono-functional, bi-functional, tri-functional or tetra-functional amines;
and wherein R2 and R3 are selected from group consisting of all possible bi-functional, tri-functional or tetra-functional amines and wherein R1 is equal to or different than R2 and R3;

and wherein R2 is equal to or different than R3;
and where n is an number 10 to 100;
and where m is an number equal to or different than n.

For the one step synthesis of polyfunctional amines, it is possible to provide a combination of amines. The combination can be mono/bi, mono/tri, mono/tetra or bi/bi, bi/tri, bi/tetra, tri/tri, tri/tetra and tetra/tetra for tri-glycidyl monomer, and can be bi/bi, bi/tri, bi/tetra, tri/tri, tri/tetra and tetra/tetra for bi-glycidyl monomer. Combinations of mono/mono will not provide the required moieties for the present disclosure.

To make the reactions in the current disclosure work, proper ratios between glycidyl monomers to amine monomers, ratios among all amines when combinations of amines are involved and ratios among all glycidyl monomers when combinations of glycidyl monomers are used need to be controlled. The following relations have to be true for construction of desired polyamine in this disclosure:

1. Reaction between triglycidyl monomer and single bi, tri and tetra amines, or combinations of bi/bi, bi/tri, bi/tetra, tri/tri, tri/tetra and tetra/tetra amines:

$M_a/M_g = 2n+1$

2. Reaction between triglycidyl monomer and combination of mono/bi amines:

$M_a/M_g = 2n+1$, and $M_{bia}/M_g >= 1-1/n$

3. Reaction between triglycidyl monomer and combination of mono/tri amines $M_a/M_g = 2n+1$, and $2M_{tria}/M_g >= 1-1/n$ 4. Reaction between triglycidyl monomer and combination of mono/tetra amines $M_a/M_g = 2n+1$, and $3M_{tetra}/M_g > 1-1/n$ 5. Reaction between biglycidyl monomer/combination of biglycidyl monomers and single bi, tri, tetra amines, or combinations of bi/bi, bi/tri, bi/tetra, tri/tri, tri/tetra and tetra/tetra amines:

$M_a/M_g = n+1$

6. Reaction between biglycidyl monomer/combination of biglycidyl monomers and combination of mono/tri amines:

$M_a/M_g = n+1$, and $2M_{tria}/M_g >= 1-1/n$

7. Reaction between biglycidyl monomer/combination of biglycidyl monomers and combination of mono/tetra amines:

$Ma/Mg = n+1$, and $3Mt_{etraa}/M_g > 1-1/n$

Where: $M_a$: molar amount of total amine used in reaction.
$M_g$: molar amount of total glycidyl monomer used in reaction.
$M_{bia}$: molar amount of total biamine used in reaction.
$M_{tria}$: molar amount of total triamine used in reaction.
$M_{tetraa}$: molar amount of total tetraamine used in reaction.
n: designed polymerization degree of polyfunctional amine.

Reaction Type II: Two-Step Process

Oligomeric one step polyfunctional amines prepared from the reaction between tri-glycidyl monomer and a bi, a, tri-, and a tetra functional amine, or combinations of bi/bi, bi/tri, bi/tetra, tri/tri, tri/tetra and tetra/tetra amines, or between bi glycidyl monomer and a tri or tetra amine, or combinations of bi/tri, bi/tetra, tri/tri, tri/tetra or tetra/tetra amines carry —NH or —NH$_2$ groups. A further aspect of the present disclosure include treatment of the obtained oligomeric with glycidyl alkenyl compounds to prepare alkenyl functional oligomeric polyamine (I-x-ene), and copolymerization of I-x-ene with other water soluble alkenyl monomers lead to two-step polyfunctional amine with increased molecular weight, generalized by formula (II-x).

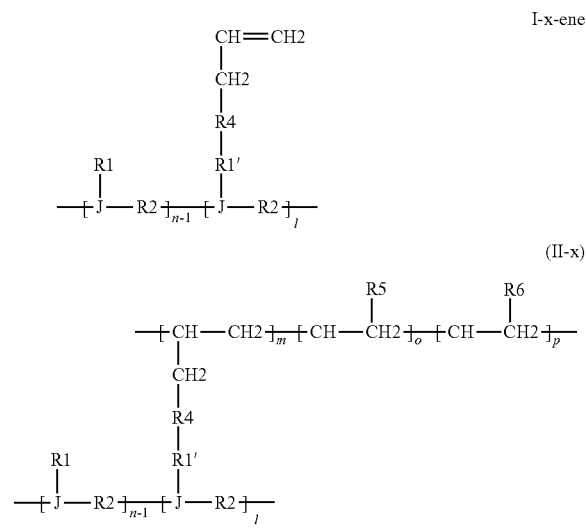

Where the substituent J, is the result of a ring-opening reaction during nucleophilic substitution of a bi- or tri-glycidyl moiety;

And wherein R1 and R2 are selected from the group consisting of a full list of bi, tri or tetra functional amines, or combination of bi/bi, bi/tri, bi/tetra, tri/tri, tri/tetra and tetra/tetra amines for triglycidyl monomer, and are selected from the group consisting of a full list of tri or tetra functional amines, or combination of bi/tri, bi/tetra, tri/tri, tri/tetra and tetra/tetra amines for diglycidyl monomers;

and wherein proton loss of R1 in its —NH or —NH$_2$ site results in R1';

and wherein R4 is the connecting group between polyamine body and the alkene functionality. If AGE is employed in this preparation, the connecting group is —CH$_2$CH(OH)CH$_2$O—. Variations in R4 may be created from each different connecting glycidyl alkenyl compound. Potentially, the connecting glycidyl alkenyl compound can be selected from one of the following: allyl glycidyl ether, vinyl glycidyl ether, vinyl cyclohexene oxide, glycidyl methacrylate, glycidyl acrylate, glycidyl acrylamide, and glycidyl methacrylamide.

and wherein n–1 is an number from four to nineteen;
and wherein m is an number from 1 to 100;
and wherein o is an number from 1 to 100;
and wherein p is an number from 1 to 100;
and wherein repeating unit carrying R5 is resulted from polymerization of a water soluble monomer having a carbon to carbon double bond, C=C, that is preferably an acrylic acid or acrylic acid derivative;
and wherein repeating unit carrying R6 is resulted from polymerization of a water soluble monomer having a carbon to carbon double bond, C=C, preferably acrylamide or a derivative of acrylamide;
and where the resulting structure is greater than or equal to 50,000 Daltons.

An extension list for water soluble alkenyl co-monomer includes: acrylamide, methacrylamide vinyl acetate, acrylic acid, methacrylic acid, ethacrylic acid, maleic acid, fumaric acid, styrene sulfonic acid, methyl acrylate, methyl methacrylate, ethyl acrylate, 2-acrylamido-2-methylpropane sulfonic acid, N-isopropylacrylamide, hydroxyethyl methacrylate, N,N-dimethylaminoethyl methacrylate, N,N-dimethylpropyl methacrylate, N,N-dimethylbutyl methacrylate, aminoethyl methacrylate.

The anionically stabilized latex binders used to provide the crosslinkable polymer latexes of the present disclosure are primarily formed by the reaction of three separate acrylic (styrene free) monomers—butyl acrylate (BA), methyl methacrylate (MMA) and methacrylic acid (MAA). Preparation of the latex binders were performed as discussed in the appropriate section on preparation of crosslinkable polymer latexes below.

The full, final, shelf-stable aqueous polymer latex coating composition (polymer) comprises anionically stabilized latex binders derived from the seed of Table 1 (shown below in the Method of Making Crosslinkable Latex Polymers Section below), exhibiting a glass transition temperature (Tg) of 20 to 40° C.; more preferably, 25 to 30° C., and most preferably 25 to 27° C. The ammonium hydroxide is added in an amount that effectively raises the pH of the aqueous composition immediately after the latex is prepared. As the pH of the final latex composition reaches a range of 9.5 to 10.5, the addition of the polyfunctional oligomeric/polymeric amine crosslinker occurs, therefore preventing the trigger of the cross-linking activity with the final latex paint formulation during storage.

Additional formulae for fast dry latexes have been previously presented in US patent application No. 2014/0079888 which is hereby fully incorporated by reference.

To summarize, the final latex polymer emulsion composition of the present disclosure comprises;
(a) either the use of the constituents listed in Table 1 for seeding the latex and preparing the latex binder or the use of another anionically stabilized latex—the formula of which is an extension of those found in US patent application no. 2014/0079888
(b) a water soluble polyamine solution where the polyamine concentration varies between 10%-15%, which is made from the polymerization reaction between glycidyl monomers and amine functional monomers (with or without further treatment of glycidyl alkenyl compounds).
(c) ammonium hydroxide
(d) $TiO_2$ as pigment and $CaCO_3$ as filler
(e) auxiliary additives as needed—including co-solvents, plasticizers, deformers and thickeners.

The present disclosure describes a high build, fast drying, and fast hardening aqueous coating composition comprising: (a) an anionically stabilized polymer latex binder comprising: (i) 35 to 65% by weight, based on the latex binder weight; (ii) 25 to 55% by weight, based on the latex binder weight; and (iii) 0.5 to 15% by weight, based on the latex binder weight, r; (iv) 0.1% to 4% by weight, based on the latex binder weight, of at least one anionic surfactant; and the use of (v) 0.5 and 1.5% polyfunctional amine crosslinker, wherein the latex binder has a glass transition temperature less than 45 degrees Centigrade, when the latex binder has been applied to the appropriate surface and has an average particle diameter size of between 100 nanometers and 300 nanometers.

Formation of the water soluble polyfunctional amines is accomplished by the nucleophilic substitution ring opening reaction between glycidyl monomers and amino monomers.

The composition of the bi- and/or tri-glycidyl monomers can include each of the following reactants and subsequent moieties; triglycidyl isocyanurate (TGIC), poly(propylene glycol) diglycidyl ether, poly(ethylene glycol) diglycidyl ether, resorcinol glycidyl ether, neopentyl diglycidyl ether, butanediol diglycidyl ether. In the present disclosure, the use of TGIC is the primary choice and all compositions of the polyfunctional oligomeric and polymeric amines disclosed herein are based upon reactions with this glycidyl group, but this is not a limitation of the present disclosure. Both the molecular weight and the molecular structure of the polyfunctional oligomeric amines are controlled by the stoichiometric ratio of the total amount of glycidyl groups to that of the amino functional groups. This is also the ratio of each amine among amine combinations, and the ratio of each glycidyl monomer among combinations of glycidyl monomers. In this disclosure, mono-functional, bi-functional, tri-functional and tetra-functional amines or combinations of these may be used for the preparations shown. A complete listing of possible amines has been presented above.

To achieve the appropriate molecular weight for the polyfunctional oligomeric amines to be used for the present disclosure, a proper stoichiometric ratio between amine functional monomers and epoxy functional monomers needs to be controlled. For example, for structural formula (I-x-1), the ratio of glycidyl compounds to di-amine compounds is $n:(2n+1)$. For the structural formula (I-x-2), the ratio of glycidyl to mono to di-amine compounds is $n:(n+1):n$. For the structural formula (I-x-3), the ratio of glycidyl to diamine compounds is $n:(2n+1)$. However, kinetic factors also play a role in the reactions between trifunctional glycidyl monomers and tetra functional amines when attempting to ensure full water solubility of these compounds.

Polymerization between glycidyl monomers and amine monomers gives rise to polyfunctional amine structures. Above, it was noted that there are functional groups for building molecular weight associated with these polyfunctional amines. More specifically, the amino groups in the polyfunctional amine can themselves be categorized as two separate groups. The structural amine and/or amino groups, which can be secondary or tertiary, stem from the glycidyl ring opening reaction resulting from the monomeric amine in a nucleophilic substitution reaction. The functional amine groups allow for ionic interaction between the latex binder particles and the polyfunctional amine crosslinkers. Structural amino groups are sterically hindered and always exhibit decreased pKb compared to what they would normally exhibit in their simple monomeric state. These groups therefore possess very little capability to interact with anionically stabilized latex particles. Instead they only serve as molecular weight building blocks for the polyfunctional amines. On the contrary, the functional amines, which are either intended to be left unreacted or reacted but distribute peripherally with the polyfunctional amines, either possesses much stronger pKb values or are sterically approachable by the anionically stabilized latex particles. They are much more capable of providing crosslinker-latex reactivity when being triggered by the pH change.

The present disclosure involves the use of crosslinkers for final latex polymer compositions containing at least one polyfunctional amine primarily acting as a physical interaction component for ionic bonding. In some cases, the structural components may also act as interactive components if the structure of the polyfunctional amine is strictly linear. Examples of the resulting polyfunctional amines of the present disclosure are schematically represented below;

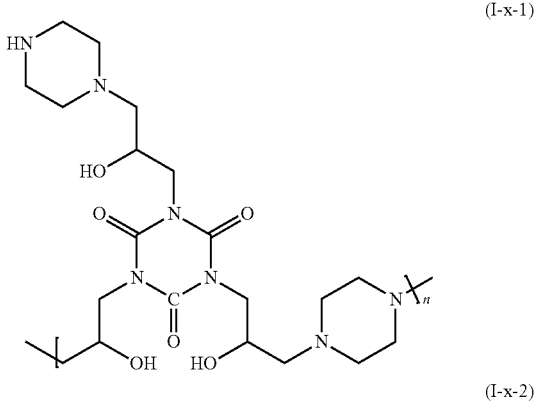

(I-x-1)

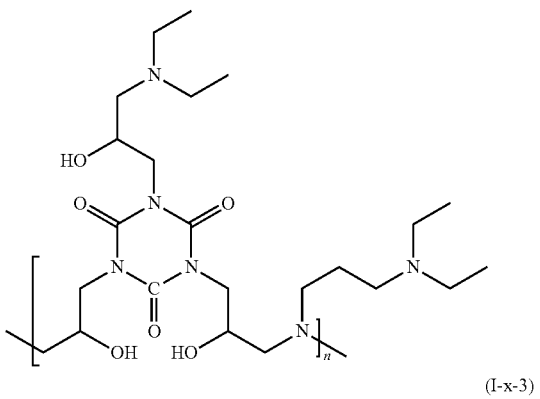

(I-x-2)

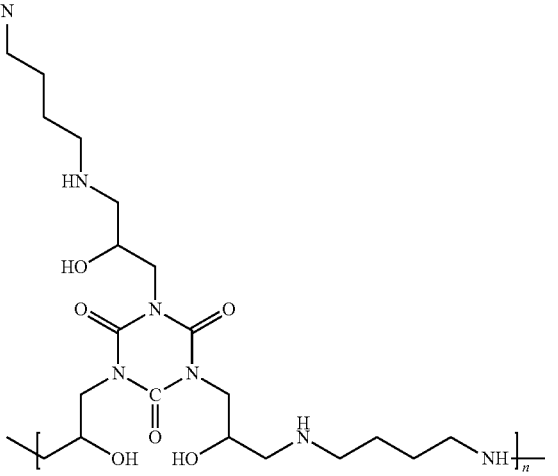

(I-x-3)

A general method for achieving the reaction leading to the oligomeric polyfunctional amine as represented above is as follows;

A solution of piperazine is charged to a 2 liter reactor and an appropriate amount of rinsing water is used to ensure that no residual remains. This solution is heated to 40 C. Into this 2 liter reactor, TGIC is added and rinsing water is used to ensure full completion. The TGIC, as a white powder, is dissolved gradually into the piperazine solution at a temperature range of between 10 and 100 C and most preferably at or above 40 C. The reaction temperature was maintained at 39 C. for another hour. AGE was added to the reactor in one portion and at one time. The reaction was allowed to remain at room temperature for another 20 minutes.

More specifically, for the synthesis of the structure of oligomer (I-x-1), the following reaction (Reaction 1) was performed;

(A)+(B)→(I-x-1), where (A) is triglycidyl isocyanurate (TGIC)

(B) is a bi-functional amine (such as piperazine), and (I-x-1) is a polyfunctional amino group with repeating units, n, of structure (I-x-1).

A solution of 12.2 g piperazine in 200.0 g water was added to a 1 liter reactor. 42.6 g water was used to rinse the addition funnel and the beaker to ensure full addition. The aqueous solution was heated to 40 C., and 20.0 g of TGIC was poured in one portion into this reactor. Some TGIC remains attached to the addition funnel and the beaker charging it, therefore 107.7 g water was added to rinse the funnel and the beaker to ensure full addition. An exothermic reaction occurred over the next 5-10 minutes to raise the temperature to 47 C. The reaction was allowed continue for 160 minutes, resulting in a clear solution that was later released from the reactor without further treatment.

REACTION 1:

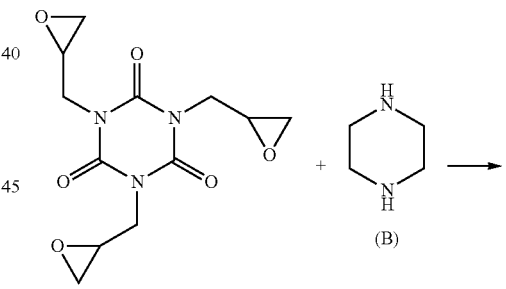

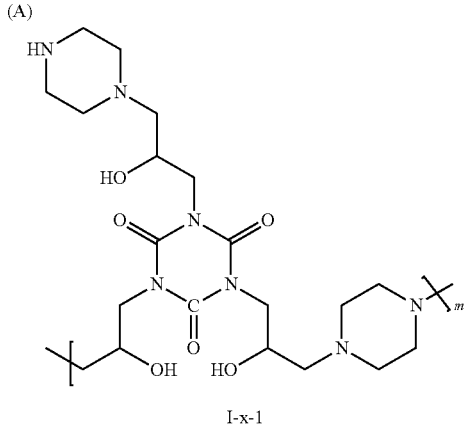

I-x-1

The synthesis of the structure of oligomer (I-x-2), as provided in Reaction 2, was performed using the following procedure;
  (A)+(C)+(D)→(I-x-2), where (A) is triglycidyl isocyanurate (TGIC)
  (C) is a bi-functional amine (such as DEAPA),
  (D) is a mono-functional amine (such as DEA), and
  (I-x-2) is a polyfunctional amine group with repeating units, n, of structure (I-b-2).

To an 800 mL beaker, 8.7 g DEAPA, 4.97 g DEA and 200.0 g water were charged. The solution was mechanically stirred gently and carefully heated to 41 C. TGIC was added into the solution in one portion. 100.0 g water was used to rinse. The reaction was maintained for another 45 minutes and then released out without further treatment.

(E) is a tetrafunctional amine (such as DAB), and
(I-x-3) is a polyfunctional amino group with repeating units, n, of structure (I-x-3).

To an 800 mL beaker, a solution of 12.5 g DAB in 200 g water was charged. The beaker was heated on a hotplate and mechanically stirred gently. The kettle was heated to 43 C., and 20.0 g TGIC was added in one portion. 99.5 g water was used to rinse. The reaction was maintained for 30 minutes at the same temperature. Next, 1.5 g NPDGE was added by dropwise addition into the reaction kettle. The solution was held for another two and half hours and released out without further treatment.

REACTION 2:

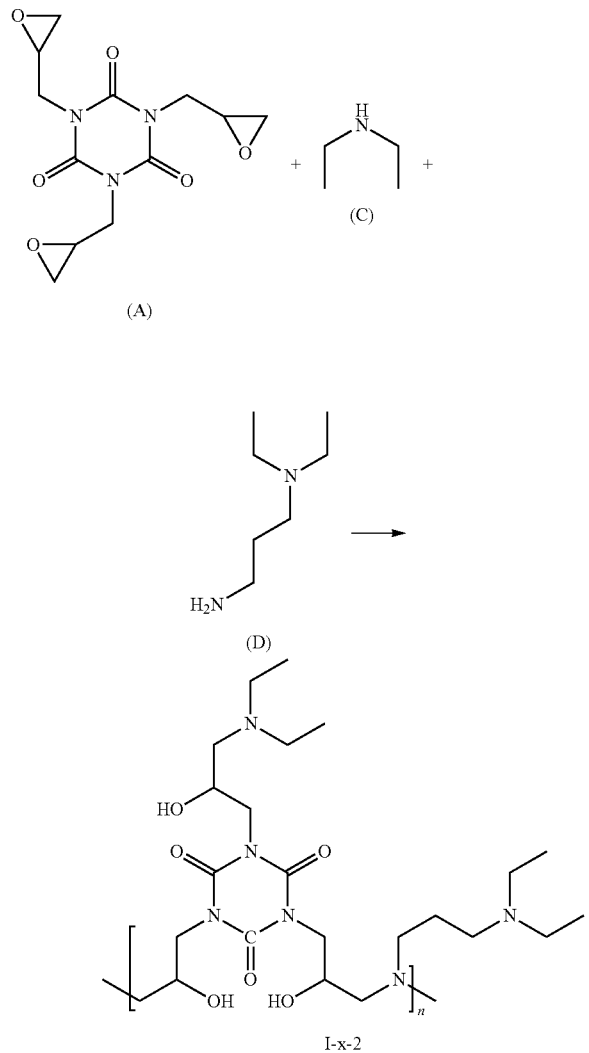

REACTION 3:

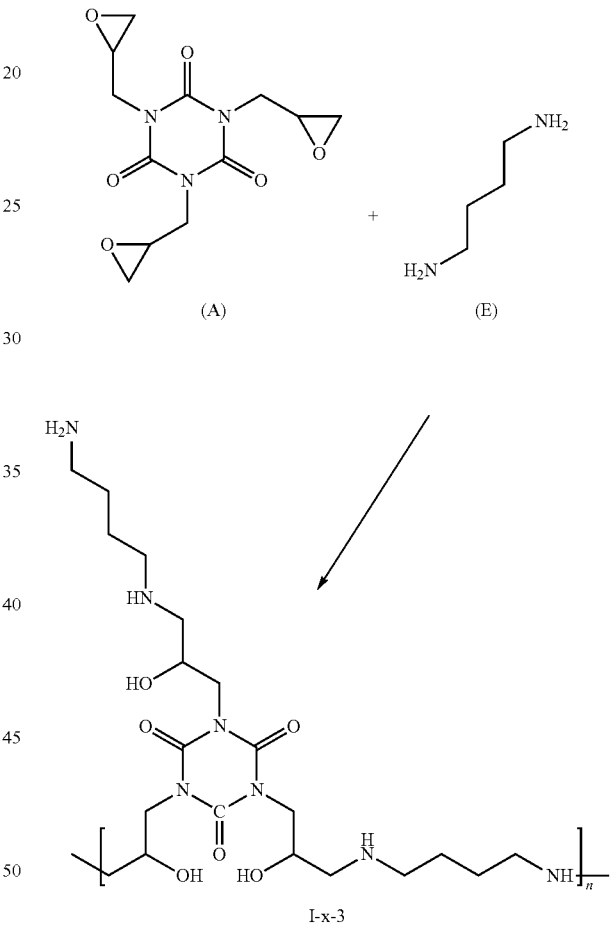

The synthesis of the structure of oligomer (I-x-3), as shown in Reaction 3, was performed using the following procedure;
  (A)+(E)→(I-x-3), where (A) is triglycidyl isocyanurate (TGIC)

The addition of the monofunctional allyl glycidyl ethers (AGEs) is in a molar amount that is always 1/n of that of the TGIC amount used in this preparation. Monofunctional allyl glycidyl ethers (AGEs) are also considered a member of the glycidyl reactive (functional) monomer groups that as the molecule introduces a site for orthogonal polymerization in the second step, as used for molecular weight expansion. Use of the AGEs allows for introducing an α,β unsaturated ethylene to the resulting oligomeric polyamine.

(I-x-1-ene)

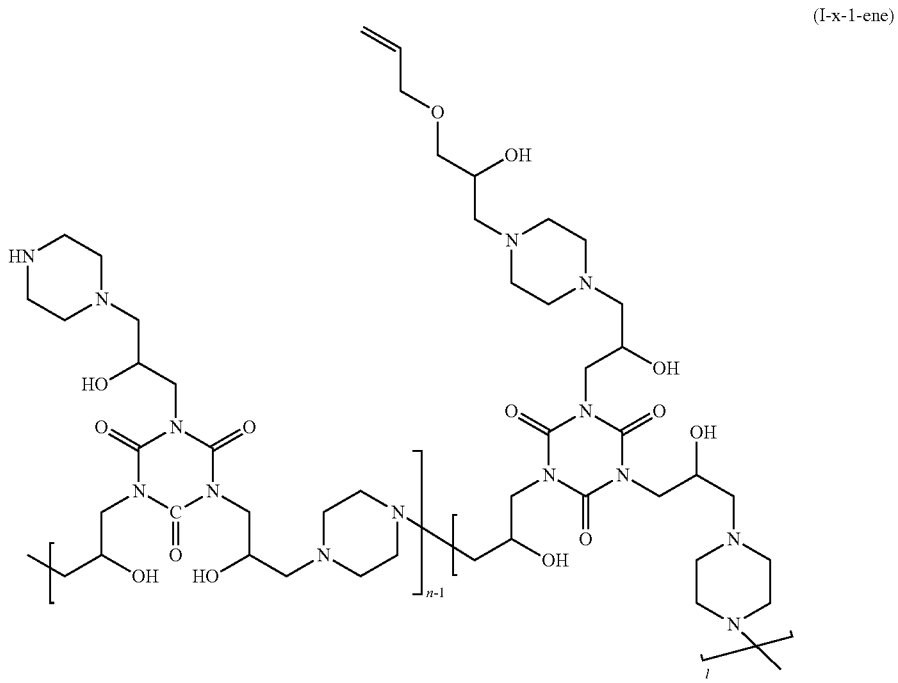

The reactants leading to the polyfunctional polymeric/oligomeric amine product shown above (I-x-1-ene), result in the introduction of an allylic double bond. Introduction of the allylic double bond serves as a monomeric moiety for the copolymerization with for example MAA and ACR, providing molecular weight building The synthesis of the structure of oligomer (I-x-1-ene), which includes the addition of allyl groups as shown in Reaction 4, was performed using the following procedure;
 (A)+(B)+(F)→(I-x-1-ene), where (A) is triglycidyl isocyanurate (TGIC)
 (B) is a bi-functional amine (such as piperazine),
 (F) is a allyl ether or allyl glycidyl ether containing molecule (such as AGE) and (I-x-1-ene) is a polyfunctional amino group with repeating units, n, of structure (I-x-1-ene).

to a 2 liter reactor, a solution of 24.35 g piperazine is charged together with an appropriate of water for rinsing. At room temperature, 40.03 g TGIC is added for which a separate appropriate amount of water was set aside for rinsing. The TGIC is a white powder at room temperature and is dissolved gradually into the piperazine solution. Within an hour, the combined solution was heated to 39 C. 1.57 g AGE was added in one portion. The reaction was allowed to remain at room temperature for another 20 minutes to cool to ambient conditions.

REACTION 4:

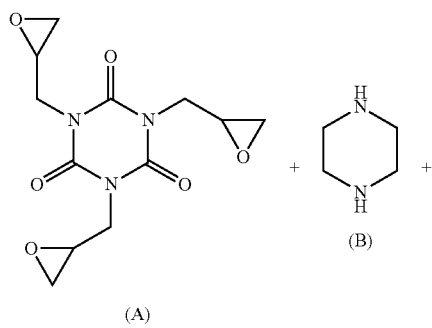

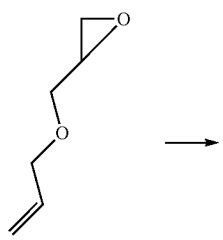

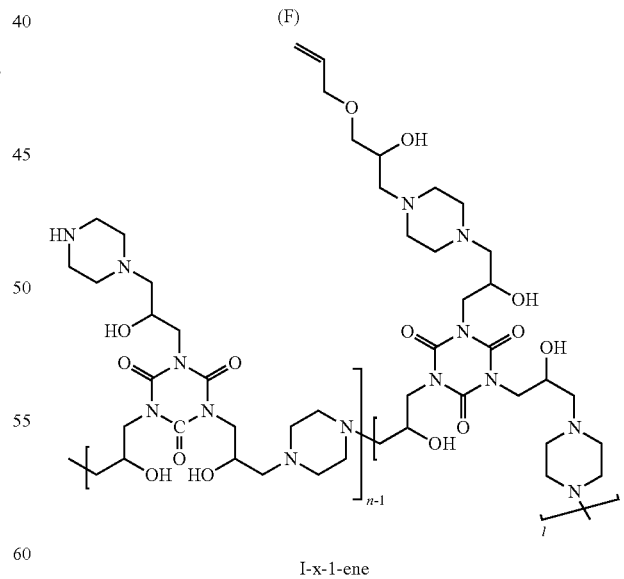

I-x-1-ene

This product is then available for a subsequent reaction with methyl acrylic acid (MAA), acrylamide (ACR), and an initiator (normally APS—ammonium persulfate) that is schematically depicted below, leading to free radical polymerization which provides a water soluble copolymer with a chain length of between 50,000 and 500,000 Dalton.

Polymerization Process for Two-Step Polyfunctional Amine Crosslinkers:

Polymerization Process for Two-Step Polyfunctional Amine Crosslinkers:

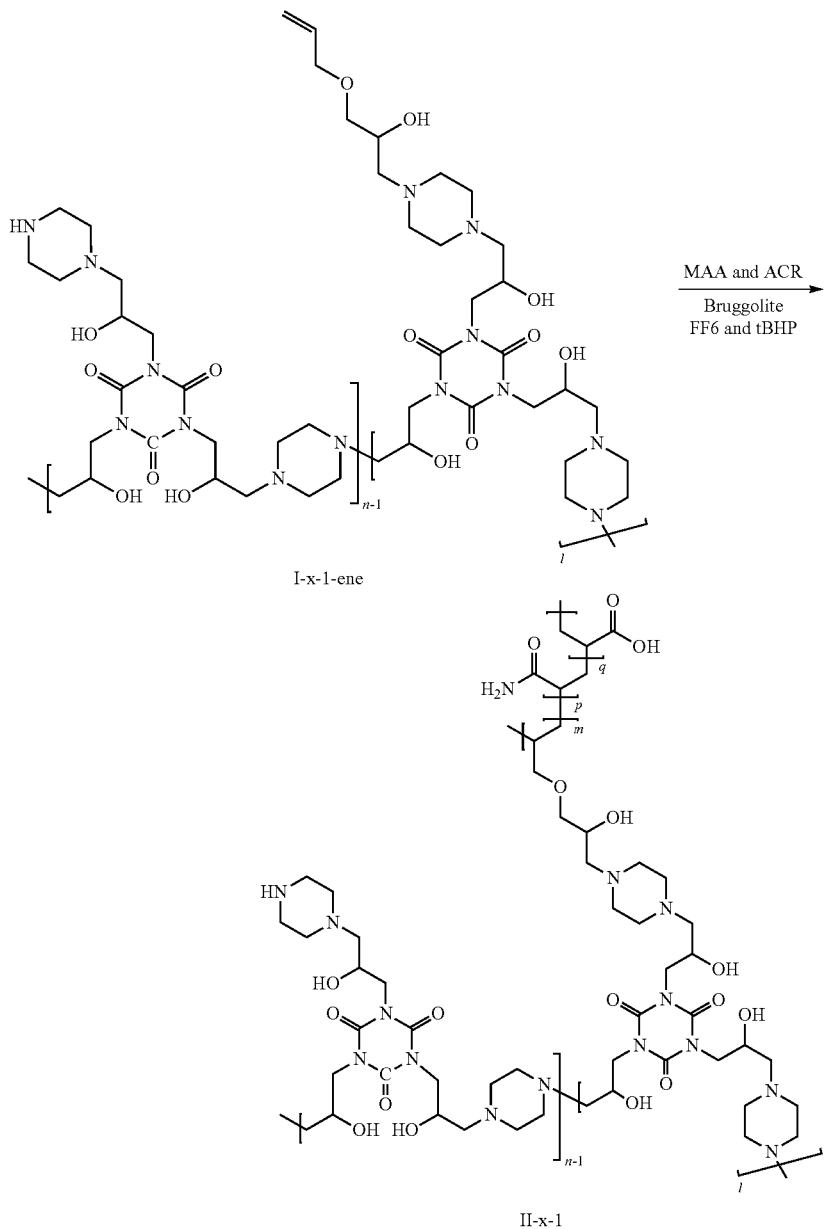

This copolymer structure (II-x-1) shown above is representative of one of a group of polyfunctional polymeric amines which possess the necessary cationic charge and molecular weight so that when placed in solution with the latex binder allows for providing a final aqueous based crosslinked polymer latex coating that forms proper films is quick drying and exhibits increased wash-off To achieve polymerization of the oligomeric polyfunctional amine the following procedure was used; 0.53 g of Bruggolite FF6 (an initiator comprised of a sodium salt of an organic sulfinic acid derivative—CAS number 401900-10-

5), together with 17.2 g acrylamide (H), and 7.1 g MAA (G) were dissolved in 30.2 g water. No chemical reaction occurs during this physical mixing process. This first solution was placed aside for later inclusion. Next, 0.37 g tBHP (70%) was added to 388.1 g of a second solution used to synthesize the polyfunctional oligomer of structure (II-x-1) shown above. Then, 40.7 g water was added to a separate 2 liter reactor and heated to 43.9 C. Into this separate reactor, the first solution and the second solution were added together over a period of 35 minutes. 7.6 g ammonium hydroxide (30%) was also added to the reactor during this addition. The final (production) solution was held at the 40-45 C. for 15 minutes to convert all unreacted monomers. The reactants were then released from the reactor and stored without further purification.

Based on the synthetic route described above, the following copolymer structures are also possible.

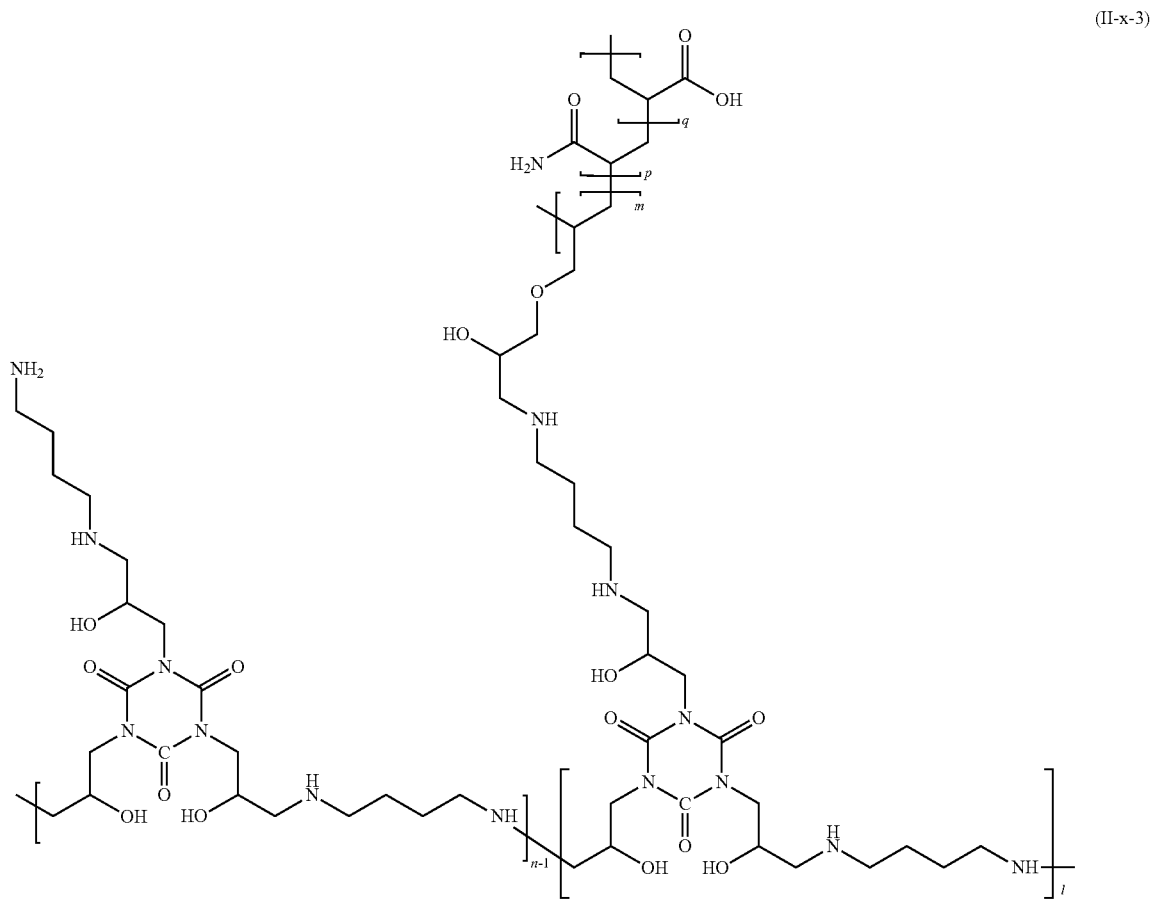

(II-x-3)

When the water soluble polyfunctional amines (shown above) are combined in solution with the latex binder, the pH of the solution (adjusted by adding ammonium hydroxide) should be at least 9.6 and preferably no greater than 10.5. This solution is a volatile basic solution in that the water and ammonium hydroxide will rapidly evaporate when the solution is applied to a substrate in the open atmosphere. After application, ammonia (as the volatile base) evaporates quickly from the paint film and the polyamine becomes protonated gradually. With water loss, the interaction between anionic latex particle and cationic polyamine is activated causing clustering of the latex particles which results in fast film formation.

The volatile base, specifically ammonium hydroxide, prevents a crosslinking of the polyfunctional co-polymeric amines with the latex binder to take place prior to substrate application. The ammonium hydroxide addition provides at least two functions—it stabilizes the polyfunctional amine copolymer crosslinkers and helps to neutralize the anionic (negative) surface charge of the latex binder. As the ammonia leaves due to volatility, it triggers electrostatic interaction between the anionically charged latex binder and the cationic polyfunctional amines.

The polymer latex formulae of the present disclosure have been modified to meet the storage and fast drying film requirements described above where interaction between polyfunctional amine crosslinker and latex binder provides rapid crosslinking when applied to surfaces. The anionically stabilized fast dry latex formulae have been prepared from semi-continuous process, which allows better control of the particle size and zeta potential.

The latex polymer compositions of the present invention exhibit latent crosslinking properties. The rate of crosslinking is controlled by stabilizing the polyfunctional amines using the volatile (ammonium hydroxide) base.

Polyfunctional Amines

Polymers having repeating units of amine/amino and glycidyl groups are useful in the practice of the present invention. Examples of amine and amino groups include, but are not limited to: dimethyl amine, diethyl amine, diethanol amine, dipropyl amine, pyrrolidine, piperidine, 1-methyl piperazine, N,N,N-trimethyl-1,2-ethane diamine, N,N,N, triethyl-1,2-ethane diamine, N-methyl-N,N-diethyl-1,2-ethane diamine, N-ethyl-N,N-dimethyl-1,2-ethane diamine, N-methyl-N,N-diethyl-1,3-propane diamine, N-ethyl-N,N-dimethyl-1,3-propane diamine, methyl amine, ethyl amine, 1-propyl amine, ethanol amine, 2-propyl amine, 1-butyl amine, 2-butyl amine, 2-methyl-2-propyl amine, piperazine, N,N-dimethyl-ethyl diamine, N,N-diethyl-ethyl diamine, N,N-dimethyl propyl diamine, N,N-diethyl-propyl diamine, N,N-dimethyl amino propylene amine, N,N-dimethyl ethylene amine, N,N-diethyl amino propylene amine, N,N-diethylamino ethylene amine, amino ethyl-piperazine, N-methyl-1,2-ethane diamine, N-ethyl-1,2-ethane diamine, N-methyl-1,3-propane diamine, N-ethyl-1,3-propane diamine, 1,2-diamine ethane, 1,3-diamino propane, 1,4-diamino butane, cadaverine, cystamine, 1,6-diamino hexane, 1,2-diamine benzene, 1,3-diamino benzene, 1,4-diamino benzene, 1,4-diamino butanol, 4,4-diamino-3-hydroxy butanoic acid, 5-amino-1,3,3-trimethylcyclohexanemethylamine, 2,2'-oxybis ethanamine, alanine, and lysine.

Bi- and/or tri-glycidyl monomers can include each of the following reactants and subsequent moieties; triglycidyl isocyanurate (TGIC), poly(propylene glycol) diglycidyl ether, poly(ethylene glycol) diglycidyl ether, resorcinol glycidyl ether, neopentyl diglycidyl ether, and butanediol diglycidyl ether. In the present disclosure, the use of TGIC is the primary choice for the glycidyl groups and all compositions of the polyfunctional amines disclosed herein are based upon reactions with this glycidyl group. Both the molecular weight and the molecular structure of the polyfunctional oligomeric amines are controlled by the stoichiometric ratio of total glycidyl reactive groups to amino functional groups, the ratio of each amine among amine combinations, and the ratio of each glycidyl monomer among combinations of glycidyl monomers.

The monofunctional amines include the following ones: dimethyl amine, diethyl amine, diethanol amine, dipropyl amine, pyrrolidine, piperidine, 1-methyl piperazine, N,N,N-trimethyl-1,2-ethane diamine, N,N,N, triethyl-1,2-ethane diamine, N-methyl-N,N-diethyl-1,2-ethane diamine, N-ethyl-N,N-dimethyl-1,2-ethane diamine, N-methyl-N,N-diethyl-1,3-propane diamine, N-ethyl-N,N-dimethyl-1,3-propane diamine, The difunctional functional amines include these ones: methyl amine, ethyl amine, 1-propyl amine, ethanol amine, 2-propyl amine, 1-butyl amine, 2-butyl amine, 2-methyl-2-propyl amine, piperazine, N,N-dimethyl-ethyl diamine, N,N-diethyl-ethyl diamine, N,N-dimethyl propyl diamine, N,N-diethyl-propyl diamine, N,N-dimethyl amino propylene amine, N,N-dimethyl ethylene amine, N,N-diethyl amino propylene amine, N,N-diethyl-amino ethylene amine. The trifunctional amines include the following ones: amino ethyl-piperazine, N-methyl-1,2-ethane diamine, N-ethyl-1,2-ethane diamine, N-methyl-1,3-propane diamine, N-ethyl-1,3-propane diamine. The tetra functional amine include these ones: 1,2-diamine ethane, 1,3-diamino propane, 1,4-diamino butane, cadaverine, cystamine, 1,6-diamino hexane, 1,2-diamine benzene, 1,3-diamino benzene, 1,4-diamino benzene, 1,4-diamino butanol, 4,4-diamino-3-hydroxy butanoic acid, 5-amino-1,3,3-trimethylcyclohexanemethylamine, 2,2'-oxybis ethanamine, alanine, and lysine.

For the one-step synthesis of polyfunctional amines, a combination of amines can be used. The combination can be mono/bi, mono/tetra, mono/tri, bi/bi, bi/tri, bi/tetra, tri/tri, tri/tetra, tetra/tetra for tri-functional glycidyl monomers, such as TGIC; the combination can be mono/tri, mono/tetra, bi/bi, bi/tri, bi/tetra, tri/tri, tri/tetra and tetra/tetra for bifunctional glycidyl monomers. As stated above, the combination of mono/mono does not provide the necessary crosslinker formulations for the present disclosure.

Method of Making Crosslinkable Latex Polymers

The latex polymer compositions of the present invention may vary in properties, depending on the end-use application. In general, the polymer component may have glass transition temperature (Tg) of 15 to 40° C. and more preferably 20 to 30° C.

The weight average molecular weight of the latex polymer compositions may vary from about 5,000 to 5,000,000 Daltons; more preferably from 20,000 to 2,000,000 and most preferably from 40,000 to 100,000. Since the polymers of the present invention become highly crosslinked upon drying, there is no substantial disadvantage to starting with very low molecular weight polymers.

A waterborne polymer composition may be prepared using the latex polymer composition of the present invention along with other known additives and may use other emulsion polymerization methodologies.

The examples below illustrate the preparation of latex polymers and waterborne polymer compositions according to the invention.

First a latex seed must be prepared. Table 1 below provides the constituents of the example of one of the procedures used that follows: A 2 liter reactor was charged 210.9 g SDS solution (14% of the total solution), 4.6 g NaHCO$_3$, 503.3 g water, 158.0 g BA, 189.5 g MMA, 6.8 g MAA and 16.2 g APS. The solution was mechanically stirred and heated to 65 C. Radical polymerization occurred immediately to raise the temperature quickly. The exotherm was controlled using 410.1 g water which was added gradually over a period of four minutes. The seed solution was allowed to react for another 130 minutes to ensure the reaction proceeds to completion. The latex particle size obtained was determined to be 51 nm.

TABLE 1

| Constituents of Monomer Emulsion for Preparation of Latex Resin | |
|---|---|
| BA | 315.9 |
| MMA | 379 |
| MAA | 13.5 |
| NaHCO3 | 0.8 |
| SDS solution (14%) | 81.92 |
| IGEPAL CA 407 | 10.2 |
| Water | 270 |

Latexes or other waterborne compositions contain small particle size seed polymers, those ranging from about 25 to about 700 nm, preferably from about 50 to about 500 nm and more preferably from about 75 to about 300 nm, represent one embodiment of the invention.

Next, it was necessary to prepare the latex. This procedure was performed as follows: a kettle was charged with 231.9 g water, 32.5 acrylic seed (23% solids) and 0.8 g sodium bicarbonate. Once charged, the kettle charge was heated to 80 C using a water bath. A solution of 2.1 g APS in 30 g water and the monomer emulsion, as indicated in Table 1, above was feed into the kettle over 195 minutes. To ensure no loss of reactants, 20 g of water was used to rinse the solution. While maintaining the temperature, the latex polymerization and resulting latex polymer binder was allowed to react for another 90 minutes to ensure reaction completion. Ammonium hydroxide, 16.1 g. (30%) was added to the polymerized latex emulsion after it was cooled to ambient conditions.

Once the latex polymerization yielding the latex binder was complete, it was possible to complete the process by producing two separate latex paints, the constituents of which are listed in Table 2. The procedure for a white latex paint, with and without crosslinkers, is provided as follows. The following examples are intended to illustrate, not limit, the invention:

EXAMPLE 1

For the paint without the crosslinker (Example 1), to a quart can containing 460.0 g of latex polymerized based on the procedure above for preparing the dry latex, 8.0 g of dispersant was added along with 5.0 g defoamer, 3.0 g surfactant, and 0.2 g biocide while stirring with a high sheer mixing blade at a moderate speed for 5 minutes. Next, a rheology agent was mixed with 1.5 g of water and added to the stirring mixture and stirred at high speed for another 5 minutes.

To this, 0.8 g ammonia was added bringing the pH to 9.6. Then pigments were added carefully while stirring at high speed for 15 minutes. After completion of the mixing and accompanying grinding, 35.0 g of solvent was added slowly and at reduced stirring speed. Then 22.0 g of the coalescent was added to the mixture, stirring continuously. Finally, 4.7 g of water was added and stirred into the mixture and the mixture was stirred for another 5 minutes until complete.

COMPARATIVE EXAMPLE 1

For the paint with the crosslinker (Comparative Example 1), to a quart can containing 460.0 g of latex polymerized based on the procedure above for preparing the dry latex, was added 30.0 g of untreated crosslinker solution and stirred for 5 minutes using a high sheer mixing blade at moderate speed. Next 8.0 g dispersant was added along with 5.0 g defoamer, 3.0 g surfactant, and 0.2 g biocide while stirring with a high sheer mixing blade at a moderate speed for 5 minutes. Next a rheology agent was mixed with 1.5 g of water and added to the stirring mixture and stirred at high speed for another 5 minutes. To this, 0.8 g ammonia was added bringing the pH to 9.6. Then pigments were added carefully while stirring at high speed for 15 minutes. After completion of the mixing and accompanying grinding, 35.0 g of solvent was added slowly and at a reduced stirring speed. Then 22.0 g of the coalescent was added to the mixture, stirring continuously. Finally, 4.7 g of water was added and stirred into the mixture and the mixture was stirred for another 5 minutes until complete.

Table 2 below summarizes the contents of the described procedure and resulting latex paint solutions;

TABLE 2

Constituents of Two Latex Paints with and without Crosslinkers: Example 1 and Comparative Example 1

| Components of Latex | Example 1 | Comparative example 1 |
|---|---|---|
| Latex | 460.0 | 460.0 |
| Crosslinker | — | 30.0 |
| Dispersant (226/35) | 8.0 | 8.0 |
| Defoamer (L-475) | 5.0 | 5.0 |
| Surfactant (CA-407) | 3.0 | 3.0 |
| Biocide (Proxel GXL) | 0.2 | 0.2 |
| Ammonia | 0.8 | 0.8 |
| Rheology agent (Natrosol 250 HBR) | 0.4 | 0.4 |
| Water | 30.0 | 5.0 |
| Pigment TiO2 | 150.0 | 150.0 |
| Pigment Extenders | 710.0 | 710.0 |
| Solvent (Methanol) | 30.0 | 30.0 |
| Coalescent (Texanol) | 20.0 | 20.0 |

To determine the effectiveness of the polyfunctional amine crosslinkers, a water wash-off test was performed to compare 30 minutes dry time for both Example 1 and Comparative Example 1 according to the procedures detailed in ASTM D711-10. The results are found in FIG. 2. The white latex paint patches on the left side are for the crosslinked version of the latex paint (Comparative Example 1) [210] vs. that of Example 1 [220] without the crosslinker.

Test Methods

Figure 3A:
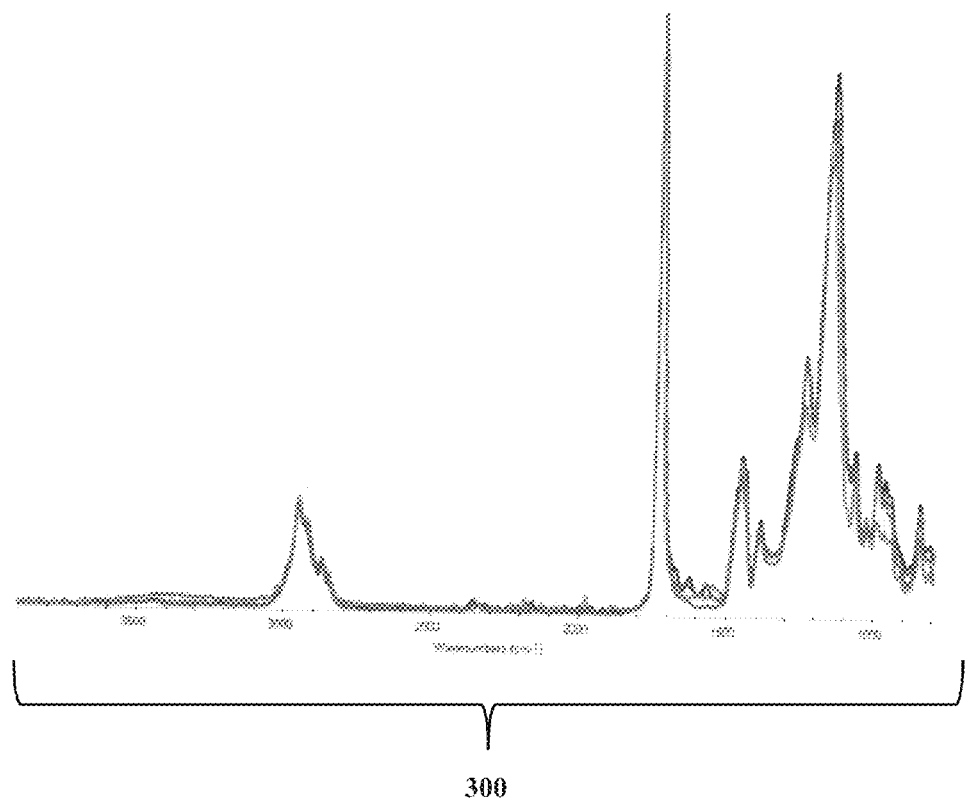
FIGS. 3a and 3b provides FTIR spectra of a latex formulation with a polyfunctional amine crosslinker of the present disclosure in comparison with other latex formulations absent these same amine crosslinkers.
Figure 3B:
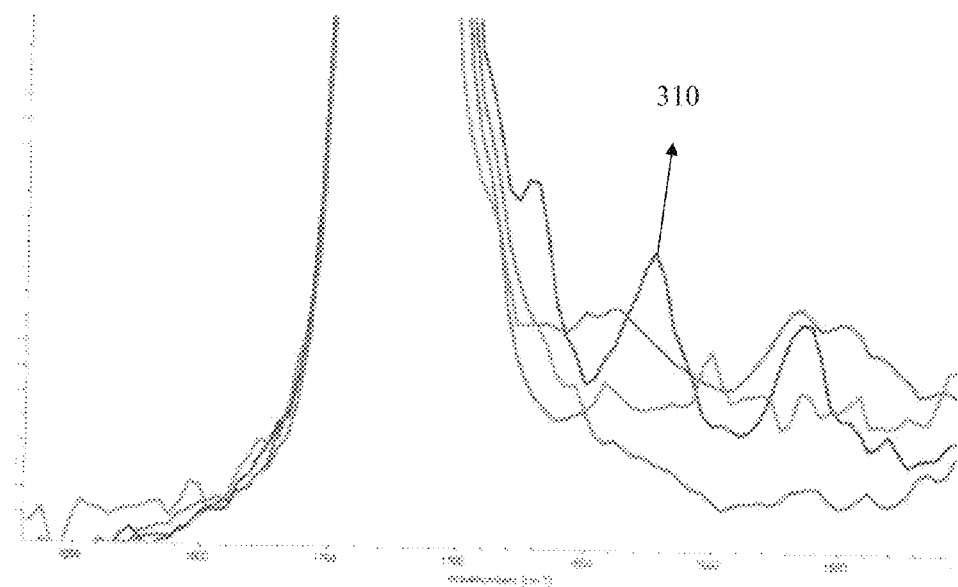

Known commercially available latex paints were sampled and compared to the latex paint of the present disclosure. FIG. 3a provides a complete visual comparison utilizing the full FTIR spectrum [300] from a standard FTIR analyzer, the Thermo Nicolet 380 for four different latex paint compositions. Three of these compositions are commercially available and the fourth represents a paint utilizing the polyfunctional amines of the present disclosure. The same data is presented in the spectrum provided within the narrower range of 1550 cm$^{-1}$ to 1870 cm$^{-1}$ wavelength, as shown in FIG. 3b (narrowed range and enlarged) which indicates the defining characteristics of the one of the compositions of the present disclosure distinguished by the characteristic peak [310] as identified and shown.

Resistance Minimum Film Forming Temperature

Resistance minimum film forming temperature (MFFT resist) is determined by casting a wet latex film with a 1-mil applicator cube on an MFFT bar set at a temperature range in which the film will coalesce during drying, pulling the edge of a brass spatula blade through the film from cold to hot end on the MFFT bar after 30 minutes, and recording the temperature at which the film offers significant resistance to the spatula.

Water-Wash Off

The water wash-off procedure generally follows ASTM D7377-08 and is modified by using section 4.6.2 of ASTM D711-10 for controlled air flow. Paint viscosity is determined by measuring Krebs Units (KU) using a paddle type viscometer. Viscosities of 80 to 90 KU are considered suitable for testing.

Drawdown Samples are Prepared Via the Procedure Provided Herein:

A sample of paint is drawn to 15 mil wet film thickness onto to a clean black scrub test panel and allowed to dry horizontally for 15 to 60 minutes in a conditioned room at 23° C.±2° C. and 50 to 55% relative humidity under a constant 2 mph air flow. When the drying time is complete, the samples are placed under a stream of 25° C. tap water flowing at a rate of 1.5 gal/min and allowed to remain there for 5 minutes, during which the time of film break through is recorded. After completion of the test, the samples are then removed from the flowing water and observed noting the percentage of wash off.

Surfactants

In the present disclosure, a combination of an anionic surfactant and a non-ionic surfactant is used. The anionic surfactant included are provided but not limited to: sodium dodecyl sulfate (SDS), ammonium dodecylsulfate (ADS), disodium salt of ethoxylated lauryl sulfosuccinate and sodium benzyl dodecyl sulfate. The nonionic surfactant includes but is not limited to IGEPAL CA-407®, Triton™ X-100 (Dow), Triton™ X-405 (Dow) and E-Sperse® 703 (Ethox).

The polymers and waterborne polymer compositions of the invention are useful in a variety of coating formulations such as architectural coatings, metal coatings, wood coatings, plastic coatings, textile coatings, cementitious coatings, paper coatings, inks, and adhesives. Examples of such coating formulations adapted for particular uses include, but are not limited to, corrosion inhibitors, concrete coatings, maintenance coatings, latex paints, industrial coatings, automotive coatings, textile backcoatings, surface printing inks and laminating inks. Accordingly, the present invention relates to such coating formulations containing a waterborne polymer composition of the invention, preferably a water-based latex. The polymers and waterborne polymer compositions of the invention may be incorporated in those coating formulations in the same manner as known polymer latexes and used with the conventional components and or additives of such compositions. The coating formulations may be clear or pigmented. With their crosslinking ability, adhesion properties, and resistance properties, the water-based latexes of the invention impart new and/or improved properties to the various coating formulations.

Upon formulation, a coating formulation containing a latex polymer or waterborne polymer composition of the invention may then be applied to a variety of surfaces, substrates, or articles, e.g., paper, plastic, steel, aluminum, wood, gypsum board, concrete, brick, masonry, or galvanized sheeting (either primed or unprimed). The type of surface, substrate, or article to be coated generally determines the type of coating formulation used. The coating formulation may be applied using means known in the art. For example, a coating formulation may be applied by spraying or by coating a substrate. In general, the coating may be dried by heating but preferably is allowed to air dry. Advantageously, a coating employing a polymer of the invention may be thermally or ambiently cured. As a further aspect, the present invention relates to a shaped or formed article which has been coated with coating formulations of the present invention.

A waterborne polymer composition according to the invention may further comprise water, along with a solvent, a pigment (organic or inorganic) and/or other additives and fillers known in the art, and enumerated below. When a solvent is used, water-miscible solvents are preferred. A latex paint composition of the invention may comprise a waterborne polymer composition of the invention, a pigment and one or more additives or fillers used in latex paints.

Additives or fillers used in formulating coatings include, but are not limited to, leveling, rheology, and flow control agents such as silicones, fluorocarbons, urethanes, or cellulosics; extenders; curing agents such as multifunctional isocyanates, multifunctional carbonates, multifunctional epoxides, or multifunctional acrylates; reactive coalescing aids such as those described in U.S. Pat. No. 5,349,026; flatting agents; pigment wetting and dispersing agents and surfactants; ultraviolet (UV) absorbers; UV light stabilizers; tinting pigments; extenders; defoaming and antifoaming agents; anti-settling, anti-sag and bodying agents; anti-skinning agents; anti-flooding and anti-floating agents; fungicides and mildewcides; corrosion inhibitors; thickening agents; plasticizers; reactive plasticizers; drying agents; catalysts; crosslinking agents; or coalescing agents. Specific examples of such additives can be found in *Raw Materials Index*, published by the National Paint & Coatings Association, 1500 Rhode Island Avenue, NW, Washington, D.C. 20005.

A polymer or waterborne polymer composition of the present invention can be utilized alone or in conjunction with other conventional waterborne polymers. Such polymers include, but are not limited to, water dispersible polymers such as consisting of polyesters, polyester-amides, cellulose esters, alkyds, polyurethanes, epoxy resins, polyamides, acrylics, vinyl polymers, polymers having pendant allyl groups such as described in U.S. Pat. No. 5,539,073, styrene-butadiene polymers, vinyl-acetate-ethylene copolymers, and the like.

The invention has been described in detail with particular reference to preferred embodiments thereof, but it will be understood that variations and modifications can be effected within the spirit and scope of the invention.

We claim:
1. Polyfunctional amines comprising recurring units derived from the reaction of one tri-glycidyl moiety and a single, di-, or tri-functional amino monomer(s), or combination of mono/bi, mono/tri, mono/tetra, bi/bi, bi/tri, bi/tetra, tri/tri, tri/tetra, and tetra/tetra functional amino monomers resulting in one or more polyfunctional amines of formula (I-x):

wherein J is a substituent that is the result of a ring-opening reaction during nucleophilic substitution of said bi- or tri-glycidyl moiety,
and wherein R1 is selected from the group consisting of: dimethyl amine, diethyl amine, diethanol amine, dipropyl amine, pyrrolidine, piperidine, 1-methyl piperazine, N,N,N-trimethyl-1,2-ethane diamine, N,N,N, triethyl-1,2-ethane diamine, N-methyl-N,N-diethyl-1,2-ethane diamine, N-ethyl-N,N-dimethyl-1,2-ethane diamine, N-methyl-N,N-diethyl-1,3-propane diamine, N-ethyl-N,N-dimethyl-1,3-propane diamine, methyl amine, ethyl amine, 1-propyl amine, ethanol amine, 2-propyl amine, 1-butyl amine, 2-butyl amine, 2-methyl-2-propyl amine, piperazine, N,N-dimethyl-ethyl diamine, N,N-diethyl-ethyl diamine, N,N-dimethyl propyl diamine, N,N-diethyl-propyl diamine, N,N-dimethyl amino propylene amine, N,N-dimethyl ethylene amine, N,N-diethyl amino propylene amine, N,N-diethyl-amino ethylene amine, amino ethyl-piperazine, N-methyl-1,2-ethane diamine, N-ethyl-1,2-ethane diamine, N-methyl-1,3-propane diamine, N-ethyl-1,3-propane diamine, 1,2-diamine ethane, 1,3-diamino propane, 1,4-diamino butane, cadaverine, cystamine, 1,6-diamino hexane, 1,2-diamine benzene, 1,3-diamino benzene, 1,4-diamino benzene, 1,4-diamino butanol, 4,4-diamino-3-hydroxy butanoic acid, 5-amino-1,3,3-trimethylcyclohexanemethylamine, 2,2'-oxybis ethanamine, alanine, and lysine;
and wherein R2 is selected from group consisting of methyl amine, ethyl amine, 1-propyl amine, ethanol amine, 2-propyl amine, 1-butyl amine, 2-butyl amine, 2-methyl-2-propyl amine, piperazine, N,N-dimethyl-ethyl diamine, N,N-diethyl-ethyl diamine, N,N-dimethyl propyl diamine, N,N-diethyl-propyl diamine, N,N-dimethyl amino propylene amine, N,N-dimethyl ethylene amine, N,N-diethyl amino propylene amine, N,N-diethylamino ethylene amine, amino ethyl-piperazine, N-methyl-1,2-ethane diamine, N-ethyl-1,2-ethane diamine, N-methyl-1,3-propane diamine, N-ethyl-1,3-propane diamine, 1,2-diamine ethane, 1,3-diamino propane, 1,4-diamino butane, cadaverine, cystamine, 1,6-diamino hexane, 1,2-diamine benzene, 1,3-diamino benzene, 1,4-diamino benzene, 1,4-diamino butanol, 4,4-diamino-3-hydroxy butanoic acid, 5-amino-1,3,3-trimethylcyclohexanemethylamine, 2,2'-oxybis ethanamine, alanine, and lysine;
and where R1 is equal to or different than R2;
and where n is a number from 10 to 100,
wherein said polyfunctional amine structure of formula (I-x) is selected from one of the general structures of formulae (I-x) and/or (I-x-a) to (I-x-f):

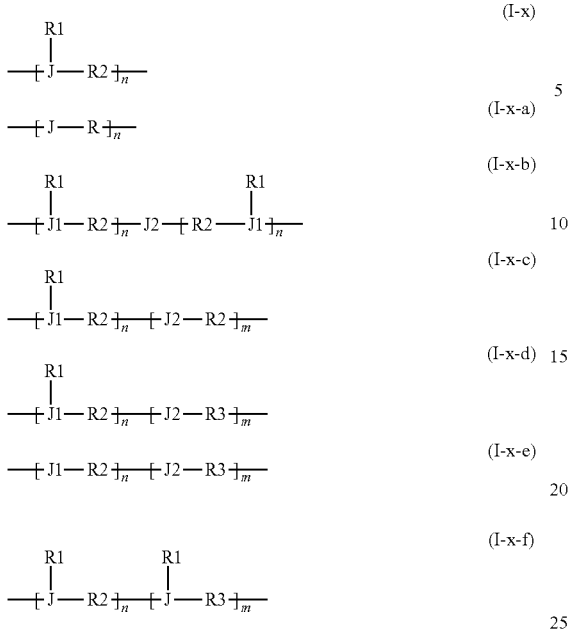

Wherein the substituents J, J1, and J2 are the result of a ring-opening reaction during nucleophilic substitution of a bi- or tri-glycidyl moiety,
and wherein J is equal to or different than J1 and J2;
and wherein J1 is equal to or different than J2;
and wherein R1 is selected from the group consisting of: dimethyl amine, diethyl amine, diethanol amine, dipropyl amine, pyrrolidine, piperidine, 1-methyl piperazine, N,N,N-trimethyl-1,2-ethane diamine, N,N,N, triethyl-1,2-ethane diamine, N-methyl-N,N-diethyl-1,2-ethane diamine, N-ethyl-N,N-dimethyl-1,3-propane diamine, methyl amine, ethyl amine, 1-propyl amine, ethanol amine, 2-propyl amine, 1-butyl amine, 2-butyl amine, 2-methyl-2-propyl amine, piperazine, N,N-dimethyl-ethyl diamine, N,N-diethyl-ethyl diamine, N,N-dimethyl propyl diamine, N,N-diethyl-propyl diamine, N,N-dimethyl amino propylene, amine, N,N-dimethyl ethylene amine, N,N-diethyl amino propylene amine, N,N-diethylamino ethylene amine, amino ethyl-piperazine, N-methyl-1,2-ethane diamine, N-ethyl-1,2-ethane diamine, N-methyl-1,3-propane diamine, N-ethyl-1,3-propane diamine, 1,2-diamine ethane, 1,3-diamino propane, 1,4-diamino butane, cadaverine, cystamine, 1,6-diamino hexane, 1,2-diamine benzene, 1,3-diamino benzene, 1,4-diamino benzene, 1,4-diamino butanol, 4,4-diamino-3-hydroxy butanoic acid, 5-amino-1,3,3-trimethylcyclohexanemethylamine, 2,2'-oxybis ethanamine, alanine, and lysine;
and R2 and R3 are selected from groups consisting of methyl amine, ethyl amine, 1-propyl amine, ethanol amine, 2-propyl amine, 1-butyl amine, 2-butyl amine, 2-lycmethyl-2-propyl amine, piperazine, N,N-dimethyl-ethyl diamine, N,N-diethyl-ethyldiamine, N,N-dimethyl propyl diamine, N,N-diethyl-propyl diamine, N,N-dimethyl amino propylene amine, N,N-dimethyl ethylene amine, N,N-diethyl amino propylene amine, N,N-diethylamino ethylene amine, amino ethyl-piperazine, N-methyl-1,2-ethane diamine, N-ethyl-1,2-ethane, diamine, N-methyl-1,3-propane diamine, N-ethyl-1,3-propane diamine, 1,2-diamine, 1,3-diamino propane, 1,4-diamino butane, cadayerine, custamine, 1,6-diamino hexane, 1,2-diamine benzene, 1,3-diamino benzene, 1,4-diamino benzene, 1,4-diamino butanol, 4,4-diamino-3-hydroxy butanoic acid, 5-amino-1,3,3-trimethylcyclohexanemethylamine, 2,2'-oxybisethanamine, alanine and lysine;
and wherein R1 is equal to or different than R2 and R3,
and wherein R2 is equal to or different than R3,
and where n is an number 10 to 100,
and where m is an number equal to or different than n,
wherein the polyfunctional amine of type formula (I-x) is a crosslinking agent bearing —NH or —NH$_2$ groups with repeating units, n that are further treated with glycidyl alkenyl compounds wherein said compounds re preferably ally glycidyl ethers; and wherein the polyfunctional amine of any formulae (I-x) and/or (I-x-a) to (I-x-f) must include —NH or —NH$_2$ group for further reaction with a glycidyl alkenyl compound that introduces an alkene group thereby forming the intermediate structure of formula (I-x-ene);

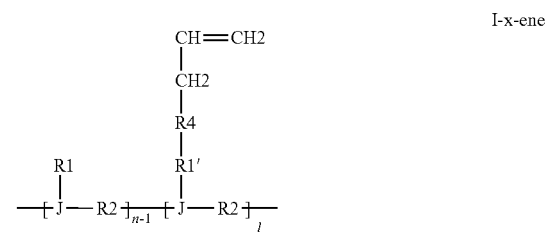

and wherein introduction of said glycidyl alkenyl compounds to said structure of formula (I-x) occurs only once per repeating unit, n, creating a repeating unit of n−1 when treated with additional polyfunctional amines.

2. Polyfunctional amine compositions of claim 1 wherein said intermediate structure of formula (I-x-ene) when reacted with MAA and ACR forms copolymers of formulae (II-x);

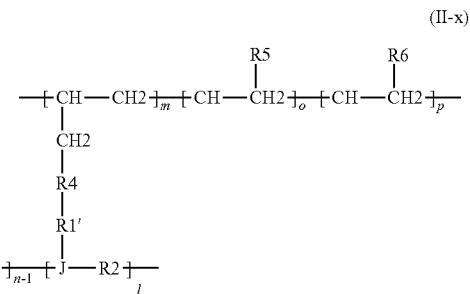

wherein substituents J, J1, and J2 are the result of a ring-opening reaction during nucleophilic substitution of a bi- or tri-glycidyl moiety,
and wherein J is equal to or different than J1 and J2;

and wherein J1 is equal to or different than J2;
and wherein R1 is selected from the group consisting of: methyl amine, ethyl amine, 1-propyl amine, ethanol amine, 2-propyl amine, 1-butyl amine, 2-butyl amine, 2-methyl-2-propyl amine, piperazine, N,N-dimethyl-ethyl diamine, N,N-diethyl-ethyl diamine, N,N-dimethyl propyl diamine, N,N-diethyl-propyl diamine, N,N-dimethyl amino propylene amine, N,N-dimethyl ethylene amine, N,N-diethyl amino propylene amine, N,N-diethylamino ethylene amine, amino ethyl-piperazine, N-methyl-1,2-ethane diamine, N-ethyl-1,2-ethane diamine, N-methyl-1,3-propane diamine, N-ethyl-1,3-propane diamine, 1,2-diamine ethane, 1,3-diamino propane, 1,4-diamino butane, cadaverine, cystamine, 1,6-diamino hexane, 1,2-diamine benzene, 1,3-diamino benzene, 1,4-diamino benzene, 1,4-diamino butanol, 4,4-diamino-3-hydroxy butanoic acid, 5-amino-1,3,3-trimethylcyclohexanemethylamine, 2,2'-oxybis ethan-amine, alanine, and lysine;
and R2 and R3 are selected from groups consisting of methyl amine, ethyl amine, 1-propyl amine, ethanol amine, 2-propyl amine, 1-butyl amine, 2-butyl amine, 2-methyl-2-propyl amine, piperazine, N,N-dimethyl-ethyl diamine, N,N-diethyl-ethyl diamine, N,N-dimethyl propyl diamine, N,N-diethyl-propyl diamine, N,N-dimethyl amino propylene amine, N,N-dimethyl ethylene amine, N,N-diethyl amino propylene amine, N,N-diethylamino ethylene amine, amino ethyl-piperazine, N-methyl-1,2-ethane diamine, N-ethyl-1,2-ethane diamine, N-methyl-1,3-propane diamine, N-ethyl-1,3-propane diamine, 1,2-diamine ethane, 1,3-diamino propane, 1,4-diamino butane, cadaverine, cystamine, 1,6-diamino hexane, 1,2-diamine benzene, 1,3-diamino benzene, 1,4-diamino benzene, 1,4-diamino butanol, 4,4-diamino-3-hydroxy butanoic acid, 5-amino-1,3,3-trimethylcyclohexanemethylamine, 2,2'-oxybis ethan-amine, alanine, and lysine;
and wherein R1 is equal to or different than R2 and R3;
and wherein R2 is equal to or different than R3;
and wherein R1' is deprotonated R1 except with a loss of a proton loss at the NH or —$NH_2$ site;
and wherein R4 is the linking group between the polyamine body of (II-x) and the alkene functionality and wherein n−1 is a number from four to nineteen;
and wherein m is a number from 1 to 100;
and wherein o is a number from 1 to 100;
and wherein p is a number from 1 to 100;
and wherein the repeating unit R5 results from polymerization of a water soluble monomer having a carbon carbon double bond, C=C, which is preferably acrylic acid or an acrylic acid derivative;
and wherein the repeating unit R6 results from polymerization of a water soluble monomer having a carbon carbon double bond, C=C, preferably acrylamide or a derivative of acrylamide;
and where the resulting structure exhibits an atomic mass that is greater than or equal to 50,000 Daltons.

3. The polyfunctional amines of claim 2, wherein when AGE is present during synthesis, said linking group is —$CH_2CH(OH)CH_2O$—, and wherein said linking group can also be a connecting glycidyl alkenyl compound that is selected from the group consisting of allyl glycidyl ether, vinyl glycidyl ether, vinyl cyclohexene oxide, glycidyl methacrylate, glycidyl acrylate, glycidyl acrylamide, and glycidyl methacrylamide.

4. Polyfunctional amines of claim 1, wherein said compositions are selected from at least one compound of the group consisting of (I-x-1), (I-x-2), and (I-x-3);

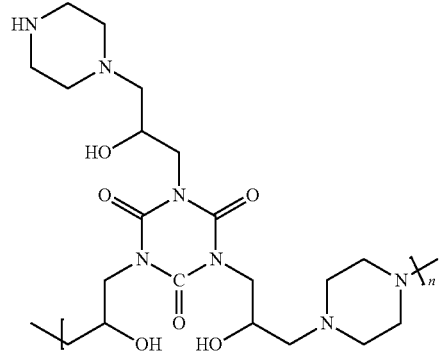

(I-x-1)

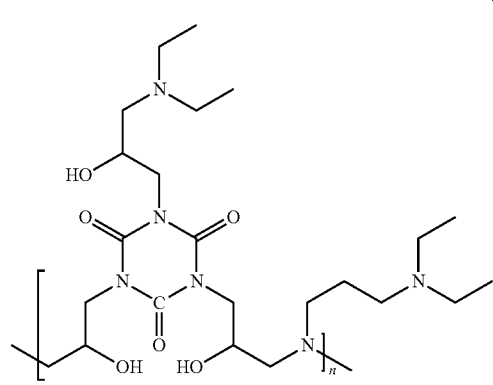

(I-x-2)

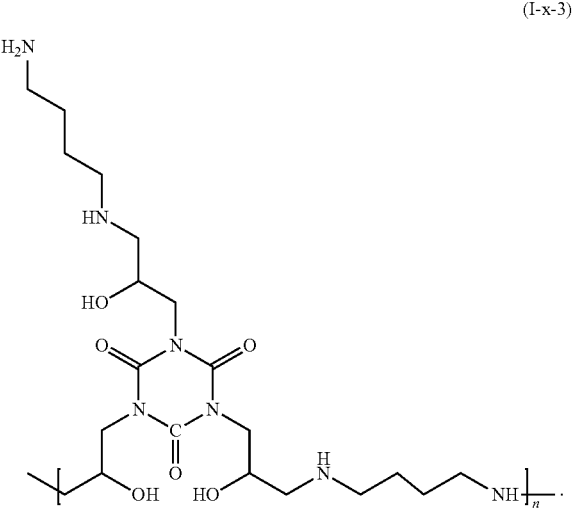

(I-x-3)

5. Polyfunctional amine compositions of claim 1 wherein said composition is an intermediate (I-x-1-ene) formed prior to the polymerization prepared with the addition of allyl glycidyl ether (AGE) resulting as formula (I-x-1);

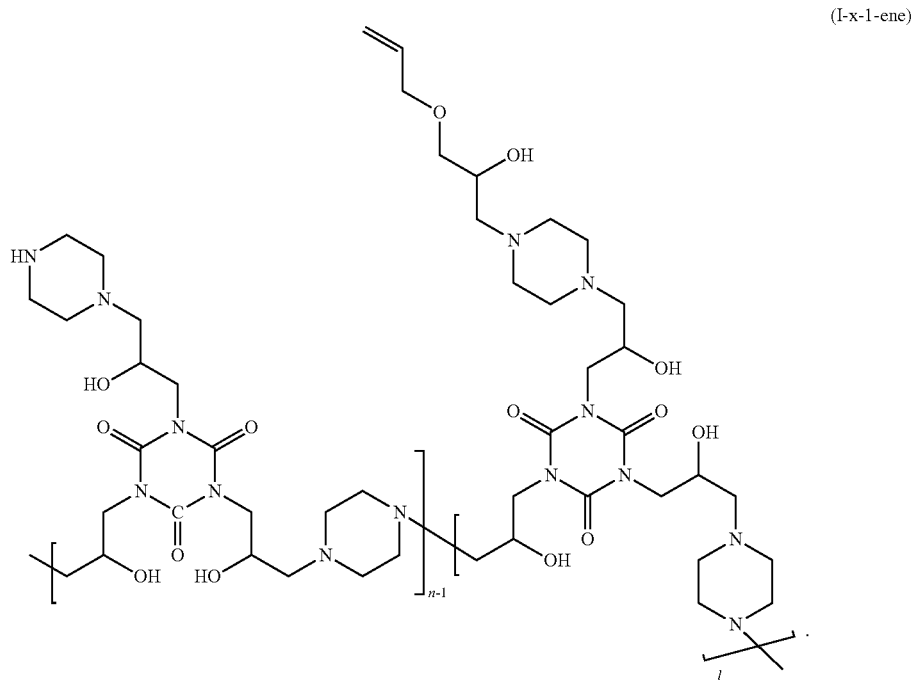
(I-x-1-ene)
6. The polyfunctional amine intermediate composition of claim 5 wherein the reaction of said intermediate with both methyl acrylic acid (MAA) and acrylamide (ACR) results in oligomeric structures (II-x-1) or (II-x-3) or modified structures thereof;
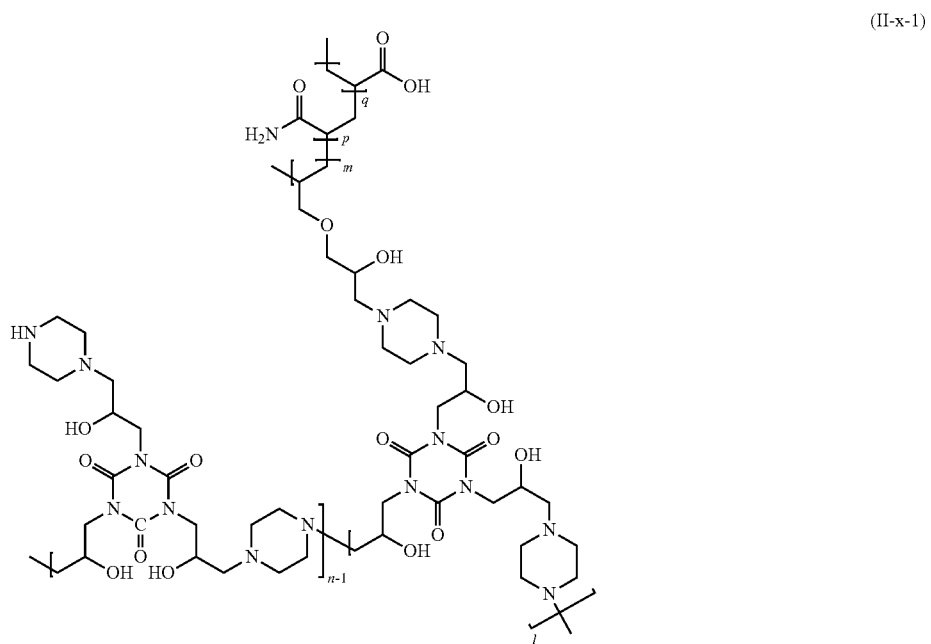
(II-x-1)

(II-x-3)

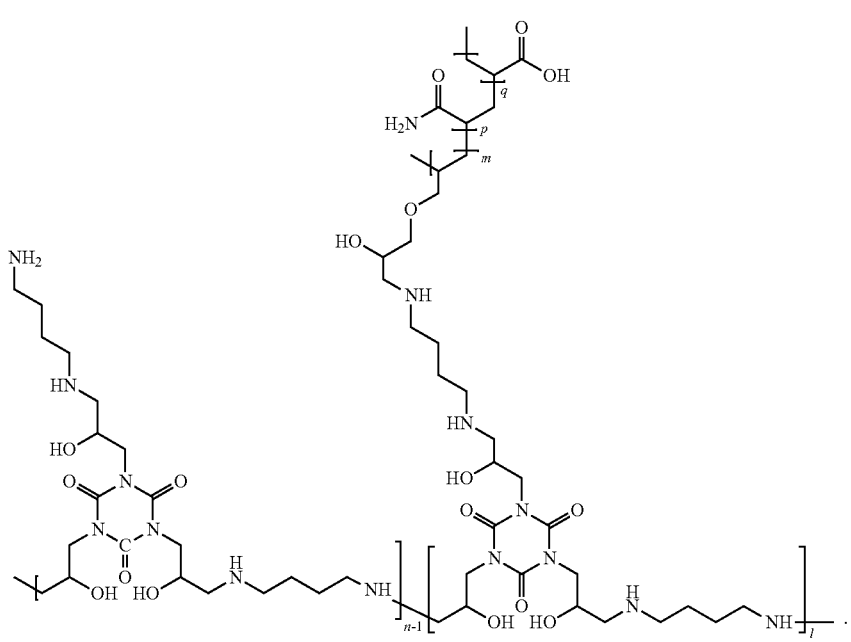

7. The synthesis of intermediate polyfunctional amines of claim 5 wherein said intermediate amines are reacted with a combination consisting of mono/bi, mono/tri, mono/tetra or bi/bi, bi/tri, bi/tetra, tri/tri, tri/tetra and tetra/tetra for tri-glycidyl monomers, and bi/bi, bi/tri, bi/tetra, tri/tri, tri/tetra and tetra/tetra for bi-glycidyl monomers.

8. The synthesis of polyfunctional amines of claim 6 wherein ratios of glycidyl monomers to amine monomers are as follows; for
   (i) the reaction between triglycidyl monomer and single bi, tri and tetra amines, or combinations of bi/bi, bi/tri, bi/tetra, tri/tri, tri/tetra and tetra/tetra amines is represented as:

$M_a/M_g = 2n+1$ (ii) the reaction between triglycidyl monomer and a combination of mono/bi amines is:
   represented as $M_a/M_g = 2n+1$, and $M_{bia}/M_g \geq 1-1/n$
   (iii) the reaction between triglycidyl monomer and a combination of mono/tri amines
   is represented as $M_a/M_g = 2n+1$, and $2M_{tria}/M_g \geq 1-1/n$
   the reaction between triglycidyl monomer and a combination of mono/tetra amines is represented as;
   $M_a/M_g = 2n+1$, and $3M_{tetra}/M_g \geq 1-1/n$
   (iv) the reaction between biglycidyl monomer/combination of biglycidyl monomers and single bi, tri, tetra amines, or combinations of bi/bi, bi/tri, bi/tetra, tri/tri, tri/tetra and tetra/tetra amines is represented as
   $M_a/M_g = n+1$
   (v) the reaction between biglycidyl monomer/combination of biglycidyl monomers and combination of mono/tri amines is represented as;

$M_a/M_g = n+1$, and $2M_{tria}/M_g \geq 1-1/n$ and (vi) the reaction between biglycidyl monomer/combination of biglycidyl monomers and combination of mono/tetra amines is represented as;

$M_a/M_g = n+1$, and $3Mt_{etraa}/M_g \geq 1-1/n$, wherein $M_a$ is the molar amount of total amine used in said reaction, $M_g$ is the molar amount of total glycidyl monomer used in said reaction, $M_{bia}$ is the molar amount of total biamine used in said reaction, $M_{tria}$ is the molar amount of total triamine used in said reaction and $M_{tetraa}$ is the molar amount of total tetra-amine used in said reaction and wherein n is the designated degree of polymerization of said polyfunctional amine.

9. The polyfunctional amines of claim 1, wherein said polyfunctional amines are crosslinking agents.

10. Polyfunctional amines of claim 1 wherein said amines are selected from at least one compound from the group consisting of formulae (I-x) and/or (I-x-a-I-x-f) also comprising additional bi- or tri-glycidyl and amine moieties, wherein Ib of said formulae forms structural compounds (I-x-1), (I-x-2), and (I-x-3) and wherein said structural compounds are derived from a one-step synthesis product excluding any C=C bonds and wherein said amines also containing an —NH or —NH₂ moiety that can either be further treated to form final two-step synthesis products or be used without further treatment to form final —NH or —NH₂ containing one-step synthesis products.

* * * * *